United States Patent
Nuovo et al.

(10) Patent No.: US 9,592,007 B2
(45) Date of Patent: Mar. 14, 2017

(54) ADJUSTABLE WEARABLE SYSTEM HAVING A MODULAR SENSOR PLATFORM

(71) Applicant: Samsung Electronics Co., Ltd., Suwon-si (KR)

(72) Inventors: Frank Settemo Nuovo, Los Angeles, CA (US); Sheldon George Phillips, Glendale, CA (US)

(73) Assignee: SAMSUNG ELECTRONICS CO., LTD. (KR)

( * ) Notice: Subject to any disclaimer, the term of this patent is extended or adjusted under 35 U.S.C. 154(b) by 0 days.

(21) Appl. No.: 14/719,043

(22) Filed: May 21, 2015

(65) Prior Publication Data

US 2015/0335284 A1 Nov. 26, 2015

Related U.S. Application Data

(60) Provisional application No. 62/002,589, filed on May 23, 2014, provisional application No. 62/061,290, filed on Oct. 8, 2014.

(51) Int. Cl.
*A61B 5/00* (2006.01)
*A61B 5/0205* (2006.01)
(Continued)

(52) U.S. Cl.
CPC ............ *A61B 5/681* (2013.01); *A61B 5/0022* (2013.01); *A61B 5/0024* (2013.01);
(Continued)

(58) Field of Classification Search
CPC ..... A61B 5/681; A61B 5/0022; A61B 5/0024; A61B 5/0059; A61B 5/02055;
(Continued)

(56) References Cited

U.S. PATENT DOCUMENTS 6,595,929 B2 * 7/2003 Stivoric ............... A61B 5/0008
600/549
7,127,432 B2 10/2006 Rubin et al.
(Continued)

FOREIGN PATENT DOCUMENTS

KR 10-2012-0033526 A 4/2012
WO 90-00366 A1 1/1990

OTHER PUBLICATIONS

Notification of Transmittal of the International Search Report and the Written Opinion of the International Searching Authority, or the Declaration corresponding to International Application No. PCT/IB2015/001979, Mar. 3, 2016.
(Continued)

*Primary Examiner* — Catherine Voorhees
(74) *Attorney, Agent, or Firm* — McAndrews, Held & Malloy, Ltd.

(57) ABSTRACT

A wearable system and methods for measuring physiological data from a device worn about a body part of a user is provided comprising a base module and sensor module. The base module comprises a display and a base computing unit. The sensor module is spatially positioned relative to the base module and over a portion of the body part for measuring one or more physiological characteristics. The base module is adjustably positioned by the user relative to the sensor module such that the sensor module maintains its positioning over the body part for sufficient contact with the body part for accurate measurements of physiological data regardless of the anthropometric size of the body part.

95 Claims, 17 Drawing Sheets

(51) Int. Cl.
*A61B 5/0402* (2006.01)
*A61B 5/01* (2006.01)
*A61B 5/053* (2006.01)

(52) U.S. Cl.
CPC ........ *A61B 5/0059* (2013.01); *A61B 5/02055* (2013.01); *A61B 5/0402* (2013.01); *A61B 5/6843* (2013.01); *A61B 5/7264* (2013.01); *A61B 5/7445* (2013.01); *A61B 5/01* (2013.01); *A61B 5/0533* (2013.01); *A61B 2560/0214* (2013.01); *A61B 2560/0223* (2013.01); *A61B 2560/0247* (2013.01); *A61B 2560/0443* (2013.01); *A61B 2560/0475* (2013.01); *A61B 2562/0257* (2013.01); *A61B 2562/12* (2013.01); *A61B 2562/164* (2013.01)

(58) Field of Classification Search
CPC ... A61B 5/0402; A61B 5/6843; A61B 5/7264; A61B 5/7445; A61B 2560/0533; A61B 2560/0223; A61B 2560/0247; A61B 2560/0443; A61B 2560/0475; A61B 2562/0257; A61B 2562/164
See application file for complete search history.

(56) References Cited

U.S. PATENT DOCUMENTS

| | | | |
|---|---|---|---|
| 7,512,985 | B1 | 3/2009 | Grabarnik et al. |
| 8,504,145 | B2* | 8/2013 | Kuroda .............. A61B 5/02438 600/519 |
| 8,965,498 | B2* | 2/2015 | Katra .................. A61B 5/0537 600/382 |
| 2007/0279852 | A1 | 12/2007 | Daniel et al. |
| 2008/0294058 | A1 | 11/2008 | Shklarski |
| 2009/0048526 | A1 | 2/2009 | Aarts et al. |
| 2009/0270743 | A1 | 10/2009 | Dugan et al. |
| 2010/0076331 | A1 | 3/2010 | Chan et al. |
| 2010/0210956 | A1* | 8/2010 | Im ..................... A61B 5/02007 600/490 |
| 2010/0306854 | A1 | 12/2010 | Neergaard |
| 2011/0245630 | A1 | 10/2011 | St. Pierre |
| 2012/0030165 | A1 | 2/2012 | Guirguis |
| 2012/0065514 | A1* | 3/2012 | Naghavi .............. G06F 19/345 600/454 |
| 2013/0192050 | A1* | 8/2013 | LeMieux ................. B21J 15/28 29/524.1 |
| 2013/0211204 | A1 | 8/2013 | Caduff et al. |
| 2013/0282679 | A1 | 10/2013 | Khin |
| 2013/0318347 | A1 | 11/2013 | Moffat |
| 2013/0324072 | A1 | 12/2013 | Hsu |
| 2014/0142403 | A1* | 5/2014 | Brumback ......... A61B 5/02433 600/324 |

OTHER PUBLICATIONS

International Search Report corresponding to International Application No. PCT/IB2015/001979, Mar. 3, 2016.
Written Opinion of the International Searching Authority, or the Declaration corresponding to International Application No. PCT/IB2015/001979, Mar. 3, 2016.
Notification of Transmittal of the International Search Report and the Written Opinion of the International Searching Authority, or the Declaration corresponding to International Application No. PCT/IB2015/001559, Jan. 20, 2016.
International Search Report corresponding to International Application No. PCT/IB2015/001559, Jan. 20, 2016.
Written Opinion of the International Searching Authority, or the Declaration corresponding to International Application No. PCT/IB2015/001559, Jan. 20, 2016.
Mare et al., Hide-n-sense: preserving privacy efficiently in wireless mhealth, Mobile Networks and Applications 19.3 (Jun. 2014): 331-344. DOI: http://dx.doi.org/10.1007/s11036-013-0447-x ProQuest document ID: 1540736834 Jun. 1, 2014.

* cited by examiner

ADJUSTABLE WEARABLE SYSTEM HAVING A MODULAR SENSOR PLATFORM

RELATED APPLICATIONS

This application claims priority to U.S. Provisional Patent Application No. 62/002,589, filed May 23, 2014. This application also claims priority to U.S. Provisional Patent Application No. 62/061,290, filed Oct. 8, 2014. The above-identified applications are hereby incorporated herein by reference in their entirety.

BACKGROUND OF THE INVENTION

The disclosure relates to a wearable device for monitoring and communicating physiological information of an individual, among other things and in particular, a wearable modular sensor platform that is adjustable about a body part.

Over the years many types of watch bands, jewelry bands, magnetic health bands, bracelets and necklaces have been marketed. Wearable devices equipped with sensors are known that may track in some fashion user data, such as activity data (duration, step count, calories burned), sleep statistics, and/or physiological data (e.g., heart rate, perspiration and skin temperature). These conventional devices, however, often are very delicate and/or too flimsy or too rigid, and do not hold up well to physical exercise, fitness activities and sports, let alone the rigors of reliable sensor measurements sufficient, for example, health care monitoring on long-term basis.

Additionally, existing wearable devices have a number of disadvantages. They are generally bulky, uncomfortable and poorly suited for long-term use on an outpatient or personal basis. Such devices are also not well suited for long-term wear by infants or uncooperative patients, such as a patient with schizophrenia who may unexpectedly remove existing sensors. Nor are such wearable devices well suited for animals that are ambulatory or that require monitoring for a long period. Aside from those disadvantages, the wearable devices to date have not been suitable as a lifestyle product that also is capable of sensitive physiological and environmental measurements, processing and communications.

Another disadvantage is that existing sensors have cumbersome electrodes. As a result, such devices are generally encased in relatively large plastic shell cases and are not comfortable or suitable for wearing for more than a few hours, and as such, lack certain advantages of more suitable locations for physiological measurements. In the case of a watch, the sensors are typically located on the top of the wrist with the display. In these devices, continuous and long term wear is not practical because, among other things, using rubberized electrodes, standard metal medical electrodes and the related adhesive pads are uncomfortable, particularly when used on older users and those with sensitive skin. Continuous wearing of these devices also tends to cause skin irritation if the portion of the skin contacted is not suitably exposed to air for days or weeks during use.

Certain sensor arrangements with a wearable device can be cumbersome for another reason. For example, some measurements (e.g. skin conductance) commonly require additional electrodes that are clamped on the fingertips or that use adhesive patches separate from the wearable devices. In these circumstances, severe limits are placed on the user's ability to perform other daily tasks.

Disadvantages with such sensor arrangements are compounded by the fact that given body parts (e.g. wrist, neck, ankle, chest, waist or head) are not the same size and shape for all users. Wearable devices to date adjust asymmetrically (e.g. belt buckle-type bands). Other bands to date that are one piece bands do not address pressure (too much or too little) applied on the skin as the size of the body part increases for a larger person relative to smaller person, or vice versa. That is, these approaches to adjustment of wearable also can make the device uncomfortable to wear due to tightness or looseness when sensors are involved. Additionally, movement of the device on a body part tends to reposition sensors and displays making the measurements and display of measurements less convenient or reliable. Discomfort may lead to movement of the device out of preferred position to reduce pain or irritation of the skin. In short, movement of the device may lead to less than accurate measurements, which can be disadvantageous to a device for long term use.

A further disadvantage is that existing systems with wireless connectivity, for example, generally exhibit a short battery life. They are not suitable for continuous or long term wireless transmission for more than a few hours. Continuous physiological data collection may be necessary, however, over days, weeks and months in cases, for example, where chronic conditions exist (e.g. sleep disorders, diabetes, etc.). Existing wireless devices have a further disadvantage of being generally limited to a single user and do not support robust data collection and analysis remote of the device. In addition, existing devices generally do not provide much more than rudimentary board data analysis.

In short, devices to date do not address the size and comfort issues (e.g. flexibility, airflow, smooth contact area, skin irritation) to allow wearing of the device for continuous or long-term use in a small, compact and lightweight form factor, that is also accurate, continuously usable, and non-invasive and/or that can also consistently maintain comfortable positioning under varying user physiology and environmental conditions. Those devices also do not employ a full array of sensor capabilities (e.g., ECG, glucose, blood pressure, hydration, etc.) in a singular modular sensor platform. These sensor capabilities do not deliver reliable medical-grade readings for the less than optimal environments that such devices can be used or for the rigors of dynamic use. These devices also do not harness the insight that daily data acquisition about the body can provide the user or a healthcare professional which require suitable processing power. Suitable processing power requires adequate battery life in a wearable 24/7 device, which wearable devices do not achieve. Moreover, these devices have not confronted the privacy and security issues associated with the communication of health-related data.

BRIEF SUMMARY

According to implementations of the present invention, a wearable system and methods for measuring physiological data from a device worn about a body part of a user is provided comprising a base module and sensor module. The base module comprises a display and a base computing unit. The sensor module is spatially positioned relative to the base module and over a portion of the body part for measuring one or more physiological characteristics. The base module is adjustably positioned by the user relative to the sensor module such that the sensor module maintains its positioning over the body part for sufficient contact with the body part for accurate measurements of physiological data regardless of the anthropometric size of the body part.

BRIEF DESCRIPTION OF SEVERAL VIEWS OF THE DRAWINGS

The features and utilities described in the foregoing brief summary, as well as the following detailed description of certain embodiments of the present general inventive concept below, will be better understood when read in conjunction with the accompanying drawings of which.

Figure 1:
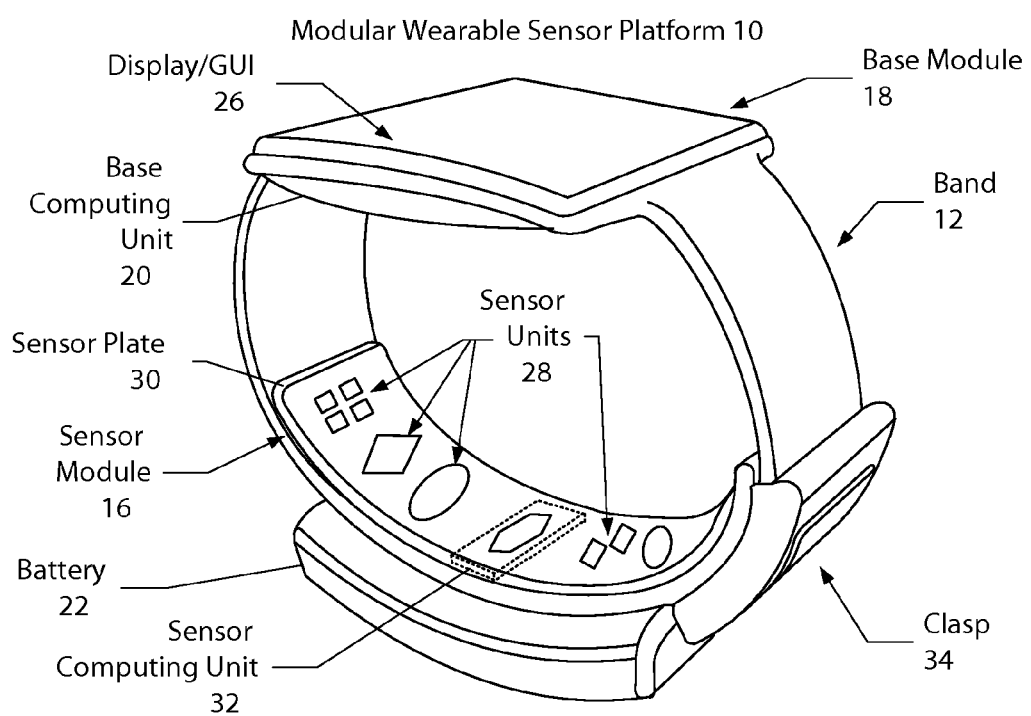
FIG. 1 is a diagram illustrating an embodiment of a modular sensor platform.

For the purpose of illustrating the general inventive concept of the invention, certain embodiments are shown in the drawings. It should be understood, however, that the present invention is not limited to the arrangements and instrumentality shown in the attached drawings.

DETAILED DESCRIPTION

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures.

Before any embodiments of the invention are explained in detail, it is to be understood that the invention is not limited in its application to the details of construction and the arrangement of components set forth in the following description or illustrated in the drawings.

Advantages and features of the present invention and methods of accomplishing the same may be understood more readily by reference to the following detailed description and the drawings. The present general inventive concept may, however, be embodied in many different forms of being practiced or of being carried out in various ways and should not be construed as being limited to the embodiments set forth herein. Rather, these embodiments are provided so that this disclosure will be thorough and complete and will fully convey the general inventive concept to those skilled in the art, and the present general inventive concept is defined by the appended claims. In the drawings, the thickness of layers and regions are exaggerated for visual clarity.

Also, the phraseology and terminology used in this document are for the purpose of description and should not be regarded as limiting. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

As should also be apparent to one of ordinary skill in the art, the systems shown in the figures are models of what actual systems might be like. Some of the modules and logical structures described are capable of being implemented in software executed by a microprocessor or a similar device, or of being implemented in hardware using a variety of components including, for example, application specific integrated circuits ("ASICs"). A term like "processor" may include or refer to both hardware and/or software. No specific meaning is implied or should be inferred simply due to the use of capitalization.

Likewise, the term "component" or "module", as used herein, means, but is not limited to, a software or hardware component, such as a field programmable gate array (FPGA) or ASIC, which performs certain tasks. A component or module may advantageously be configured to reside in the addressable storage medium and configured to execute on one or more processors. Thus, a component or module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for the components and components or modules may be combined into fewer components and components or modules or further separated into additional components and components or modules.

Unless defined otherwise, all technical and scientific terms used herein have the same meaning as commonly understood by one of ordinary skill in the art to which this invention belongs. Further, unless defined otherwise, all terms defined in generally used dictionaries should have their ordinary meaning. It is noted that the use of any and all examples, or exemplary terms provided herein is intended merely to better illuminate the general inventive concept and is not a limitation on the scope of the invention unless otherwise specified.

Embodiments of the invention relate to a system for providing a wearable device for monitoring an electrocardiogram (ECG) through a wrist of a user.

Figure 2:
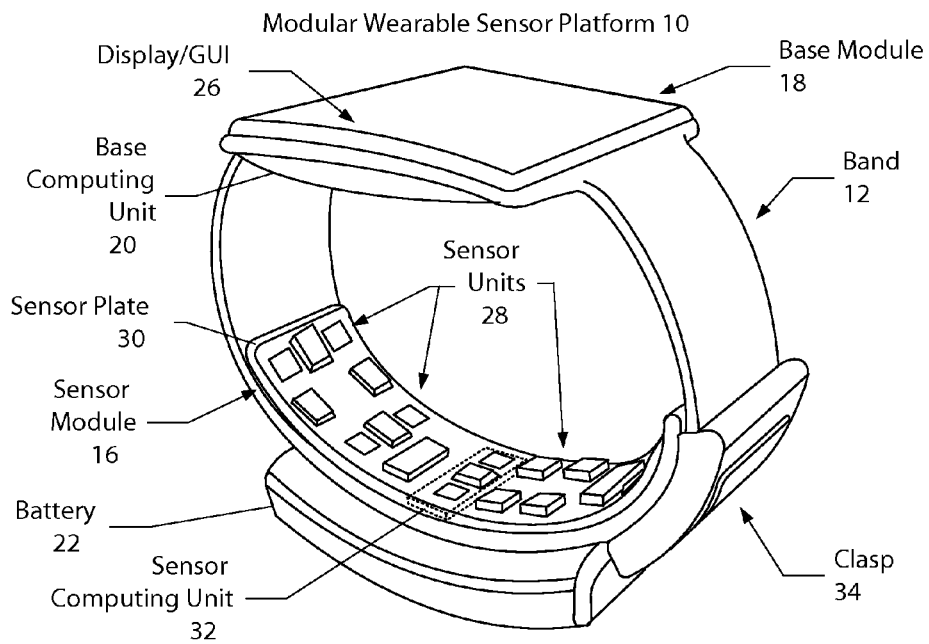
FIG. 2 is an embodiment of the modular sensor platform of FIG. 1.
Figure 3:
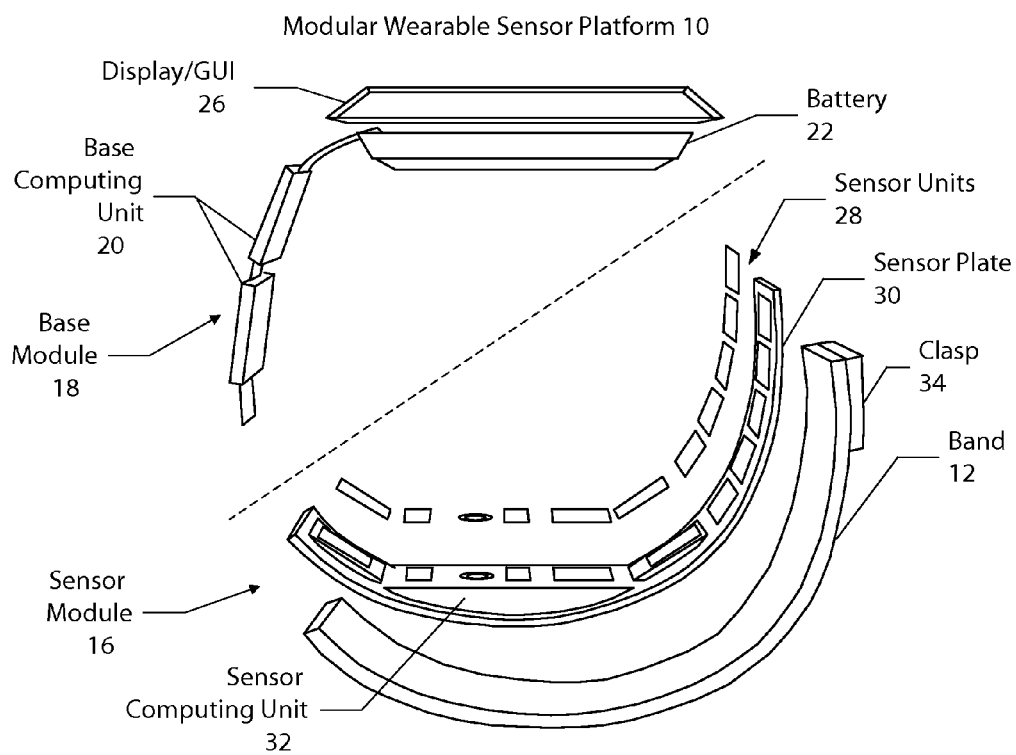
FIG. 3 is a diagram illustrating another embodiment of a modular sensor platform.

FIGS. 1 and 2 are diagrams illustrating embodiments of a modular wearable sensor platform. FIGS. 1 and 2 depict a perspective view of embodiments of the wearable sensor platform 10, while FIG. 3 depicts an exploded side view of another embodiment of the wearable sensor platform 10. Although the components of the wearable sensor platform in FIGS. 1 and 2 may be substantially the same, the locations of modules and/or components may differ.

In the embodiment shown in FIG. 1, the wearable sensor platform 10 may be implemented as a smart watch or other wearable device that fits on part of a body, here a user's wrist.

The wearable sensor platform 10 may include a base module 18, a band 12, a clasp 34, a battery 22 and a sensor module 16 coupled to the band 12. In some embodiments, the modules and/or components of the wearable sensor platform 10 may be removable by an end user (e.g., a consumer, a patient, a doctor, etc.). However, in other embodiments, the modules and/or components of the wearable sensor platform 10 are integrated into the wearable sensor platform 10 by the manufacturer and may not be intended to be removed by the end user. The wearable sensor platform 10 may be waterproof or water sealed.

The band or strap 12 may be one-piece or modular. The band 12 may be made of a fabric. For example, a wide range of twistable and expandable elastic mesh/textiles are contemplated. The band 12 may also be configured as a multiband or in modular links. The band 12 may include a latch or a clasp mechanism to retain the watch in place in certain implementations. In certain embodiments, the band 12 will contain wiring (not shown) connecting, among other things, the base module 18 and sensor module 16. Wireless communication, alone or in combination with wiring, between base module 18 and sensor module 16 is also contemplated.

The sensor module 16 may be removably attached on the band 12, such that the sensor module 16 is located at the bottom of the wearable sensor platform 10 or, said another way, on the opposite end of the base module 18. Positioning the sensor module 16 in such a way to place it in at least partial pressure contact with the skin on the underside of the user's wrist to allow the sensor units 28 to sense physiological data from the user. The contacting surface(s) of the sensor units 28 may be positioned above, at or below, or some combination such positioning, the surface of the sensor module 16.

The base module 18 attaches to the band 12 such that the base module 18 is positioned at top of the wearable sensor platform 10. Positioning the base module 18 in such a way to place it in at least partial contact with the top side of the wrist.

Figure 4:
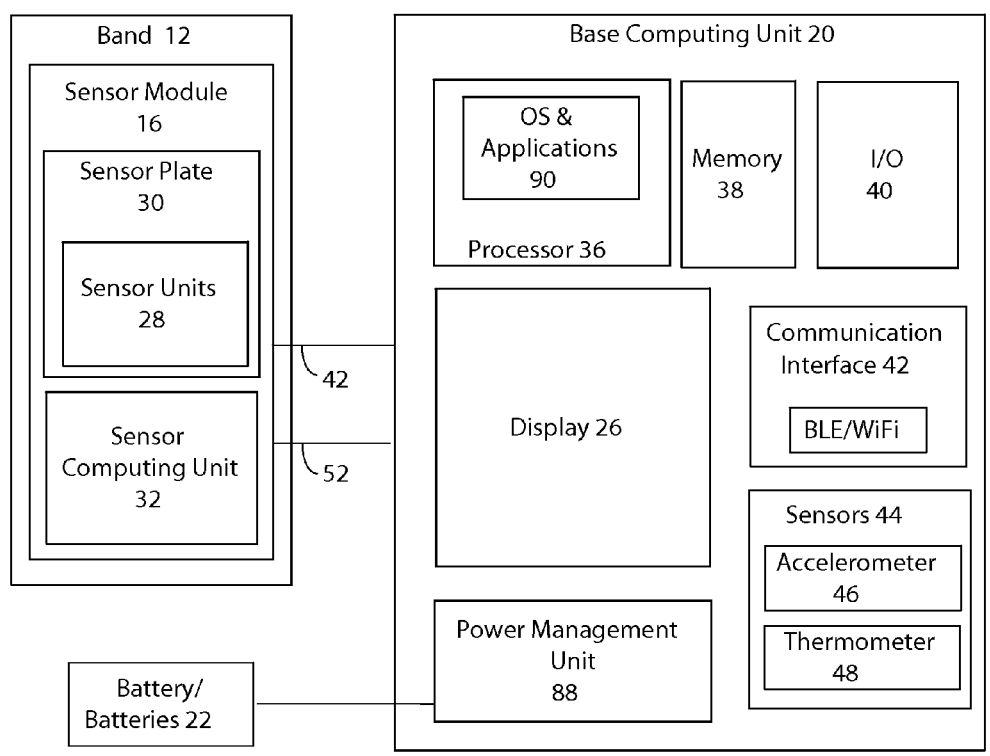
FIG. 4 is a block diagram illustrating one embodiment of the modular sensor platform, including a bandwidth sensor module in connection with components comprising the base computing unit and battery.

The base module 18 may include a base computing unit 20 and a display 26 on which a graphical user interface (GUI) may be provided. The base module 18 performs functions including, for example, displaying time, performing calculations and/or displaying data, including sensor data collected from the sensor module 16. In addition to communication with the sensor module 16, the base module 18 may wirelessly communicate with other sensor module(s) (not shown) worn on different body parts of the user to form a body area network, or with other wirelessly accessible devices (not shown), like a smartphone, tablet, display or other computing device. As will be discussed more fully with respect to FIG. 4, the base computing unit 20 may include a processor 36, memory 38, input/output 40, a communication interface 42, a battery 22 and a set of sensors 44, such as an accelerometer/gyroscope 46 and thermometer 48. In other embodiments, the base module 18 can also be other sizes, cases, and/or form factors, such as, for example, oversized, in-line, round, rectangular, square, oval, Carre, Garage, Tonneau, asymmetrical, and the like.

The sensor module 16 collects data (e.g., physiological, activity data, sleep statistics and/or other data), from a user and is in communication with the base module 18. The sensor module 16 includes sensor units 28 housed in a sensor plate 30. For certain implementations, because a portable device, such as a wristwatch, has a very small volume and limited battery power, sensor units 28 of the type disclosed may be particularly suited for implementation of a sensor measurement in a wristwatch. In some embodiments, the sensor module 16 is adjustably attached to the band 12 such that the base module 18 is not fixedly positioned, but can be configured differently depending on the physiological makeup of the wrist.

The sensor units 28 may include an optical sensor array, a thermometer, a galvanic skin response (GSR) sensor array, a bioimpedance (BioZ) sensor array, an electrocardiogram or electrocardiography (ECG) sensor, or any combination thereof. The sensors units 28 may take information about the outside world and supply it to the wearable modular sensor platform 10. The sensors 28 can also function with other components to provide user or environmental input and feedback to a user. For example, a MEMS accelerometer may be used to measure information such as position, motion, tilt, shock, and vibration for use by processor 36. Other sensor(s) may also be employed. The sensor module 16 may also include a sensor computing unit 32. The sensor units 28 may also include biological sensors (e.g., pulse, pulse oximetry, body temperature, blood pressure, body fat, etc.), proximity detectors for detecting the proximity of objects, and environmental sensors (e.g., temperature, humidity, ambient light, pressure, altitude, compass, etc.).

In other embodiments, the clasp 34 also provides an ECG electrode. One or more sensor units 28 and the ECG electrode on the clasp 34 can form a complete ECG signal circuit when the clasp 34 is touched. The sensor computing unit 32 may analyze data, perform operations (e.g., calculations) on the data, communicate data and, in some embodiments, may store the data collected by the sensor units 28. In some embodiments, the sensor computing unit 32 receives (for example, data indicative of an ECG signal) from one or more of the sensors of the sensor units 28, and processes the received data to form a predefined representation of a signal (for example, an ECG signal).

The sensor computing unit 32 can also be configured to communicate the data and/or a processed form of the received data to one or more predefined recipients, for example, the base computing unit 20, for further processing, display, communication, and the like. For example, in certain implementations the base computing unit 20 and/or sensor computing unit determine whether data is reliable and determine an indication of confidence in the data to the user.

Because the sensor computing unit 32 may be integrated into the sensor plate 30, it is shown by dashed lines in FIG. 1. In other embodiments, the sensor computing unit 32 may be omitted or located elsewhere on the wearable sensor platform 10 or remotely from the wearable sensor platform 10. In an embodiment where the sensor computing unit 32 may be omitted, the base computing unit 20 may perform functions that would otherwise be performed by the sensor computing unit 32. Through the combination of the sensor module 16 and base module 18, data may be collected, transmitted, stored, analyzed, transmitted and presented to a user.

The wearable sensor platform 10 depicted in FIG. 1 is analogous to the wearable sensor platform 10 depicted in FIGS. 2 and 3. Thus, the wearable sensor platform 10 includes a band 12, a battery 22, a clasp 34, a base module 18 including a display/GUI 26, a base computing unit 20, and a sensor module 16 including sensor units 28, a sensor plate 30, and an optional sensor computing unit 32. However, as can be seen in FIG. 3, the locations of certain modules have been altered. For example, the clasp 34 is closer in FIG. 3 to the display/GUI 26 than clasp 34 is in FIG. 1. Similarly, in FIG. 3, the battery 22 is housed with the base module 18. In the embodiment shown in FIG. 1, the battery 22 is housed on the band 12, opposite to the display 26. However, it should be understood that, in some embodiments, the battery 22 charges the base module 18 and optionally an internal or permanent battery (not shown) of the base module 18. In this way, the wearable sensor platform 10 may be worn continuously. Thus, in various embodiments, the locations and/or functions of the modules and other components may be changed.

FIG. 3 is a diagram illustrating one embodiment of a modular wearable sensor platform 10 and components comprising the base module 18. The wearable sensor platform 10 is analogous to the wearable sensor platform 10 in FIGS. 1 and 2 and thus includes analogous components having similar reference labels. In this embodiment, the wearable sensor platform 10 may include a band 12, and a sensor module 16 attached to band 12. The removable sensor module 16 may further include a sensor plate 30 attached to the band 12, and sensor units 28 attached to the sensor plate 30. The sensor module 16 may also include a sensor computing unit 32.

The wearable sensor platform 10 includes a base computing unit 20 in FIG. 3 analogous to the base computing unit 20 and one or more batteries 22 in FIG. 3. For example, permanent and/or removable batteries 22 that are analogous to the battery 22 in FIGS. 1 and 2 may be provided. In one embodiment, the base computing unit 20 may communicate with or control the sensor computing unit 32 through a communication interface 42. In one embodiment, the communication interface 42 may comprise a serial interface. The base computing unit 20 may include a processor 36, a memory 38, input/output (I/O) 40, a display 26, a communication interface 42, sensors 44, and a power management unit 88.

The processor 36, the memory 38, the I/O 40, the communication interface 42 and the sensors 44 may be coupled together via a system bus (not shown). The processor 36 may include a single processor having one or more cores, or multiple processors having one or more cores. The processor 36 may be configured with the I/O 40 to accept, receive, transduce and process verbal audio frequency command, given by the user. For example, an audio codec may be used. The processor 36 may execute instructions of an operating system (OS) and various applications 90. The processor 36 may control on command interactions among device components and communications over an I/O interface. Examples of the OS 90 may include, but not limited to, Linux Android™, Android Wear, and Tizen OS.

The memory 38 may comprise one or more memories comprising different memory types, including RAM (e.g., DRAM and SRAM) ROM, cache, virtual memory microdrive, hard disks, microSD cards, and flash memory, for example. The I/O 40 may comprise a collection of components that input information and output information. Example components comprising the I/O 40 having the ability to accept inputted, outputted or other processed data include a microphone, messaging, camera and speaker. I/O 40 may also include an audio chip (not shown), a display controller (not shown), and a touchscreen controller (not shown). In the embodiment shown in FIG. 4, the memory 38 is external to the processor 36. In other embodiments, the memory 38 can be an internal memory embedded in the processor 36.

The communication interface 42 may include components for supporting one-way or two-way wireless communications and may include a wireless network interface controller (or similar component) for wireless communication over a network in some implementations, a wired interface in other implementations, or multiple interfaces. In one embodiment, the communication interface 42 is for primarily receiving data remotely, including streaming data, which is displayed and updated on the display 26. However, in an alternative embodiment, besides transmitting data, the communication interface 42 could also support voice transmission. In an exemplary embodiment, the communication interface 42 supports low and intermediate power radio frequency (RF) communications. In certain implementations, example types of wireless communication may include Bluetooth Low Energy (BLE), WLAN (wireless local area network), WiMAX, passive radio-frequency identification (RFID), network adapters and modems. However, in another embodiment, example types of wireless communication may include a WAN (Wide Area Network) interface, Wi-Fi, WPAN, multi-hop networks, or a cellular network such as 3G, 4G, 5G or LTE (Long Term Evolution). Other wireless options may include ultra-wide band (UWB) and infrared, for example. The communication interface 42 may also include other types of communications devices (not shown) besides wireless, such as serial communications via contacts and/or USB communications. For example, a micro USB-type USB, flash drive, or other wired connection may be used with the communication interface 42.

In one embodiment, the display 26 may be integrated with the base computing unit 20; while in another embodiment, the display 26 may be external from the base computing unit 20. Display 26 may be flat or curved, e.g., curved to the approximate curvature of the body part on which the wearable sensor module platform 10 is located (e.g., a wrist, an ankle, a head, etc.).

Display 26 may be a touch screen or gesture controlled. The display 26 may be an OLED (Organic Light Emitting Diode) display, TFT LCD (Thin-Film-Transistor Liquid Crystal Display), or other appropriate display technology. The display 26 may be active-matrix. An example display 26 may be an AMOLED display or SLCD. The display may be 3D or flexible. The sensors 44 may include any type of microelectromechanical systems (MEMs) sensor. Such sensors may include an accelerometer/gyroscope 46 and a thermometer 48, for instance.

The power management unit 88 may be coupled to the power source 22 and may comprise a microcontroller that communicates and/or controls power functions of at least the base computing unit 20. Power management unit 88 communicates with the processor 36 and coordinates power management. In some embodiments, the power management unit 88 determines if a power level falls below a certain threshold level. In other embodiments, the power management unit 88 determines if an amount of time has elapsed for secondary charging.

The power source 22 may be a permanent or removable battery, fuel cell or photo voltage cell, etc. The battery 22 may be disposable. In one embodiment, the power source 22 may comprise a rechargeable, lithium ion battery or the like may be used, for example. The power management unit 88 may include a voltage controller and a charging controller for recharging the battery 22. In some implementations, one or more solar cells may be used as a power source 22. The power source 22 may also be powered or charged by AC/DC power supply. The power source 22 may charge by non-contact or contact charging. In one embodiment, the power management unit 88 may also communicate and/or control the supply of battery power to the removable sensor module 16 via power interface 52. In some embodiments, the battery 22 is embedded in the base computing unit 20. In other embodiments, the battery 22 is external to the base computing unit 20.

Other wearable device configurations may also be used. For example, the wearable system 10 can be worn on the upper arm, waist, finger, ankle, neck chest or foot for example. That is, the wearable sensor module platform 10 can be implemented as a leg or arm band, a chest band, a wristwatch, a head band, an article of clothing worn by the user such as a snug fitting shirt, or any other physical device or collection of devices worn by the user that is sufficient to ensure that the sensor units 28 are in contact with approximate positions on the user's skin to obtain accurate and reliable data.

Figure 5:
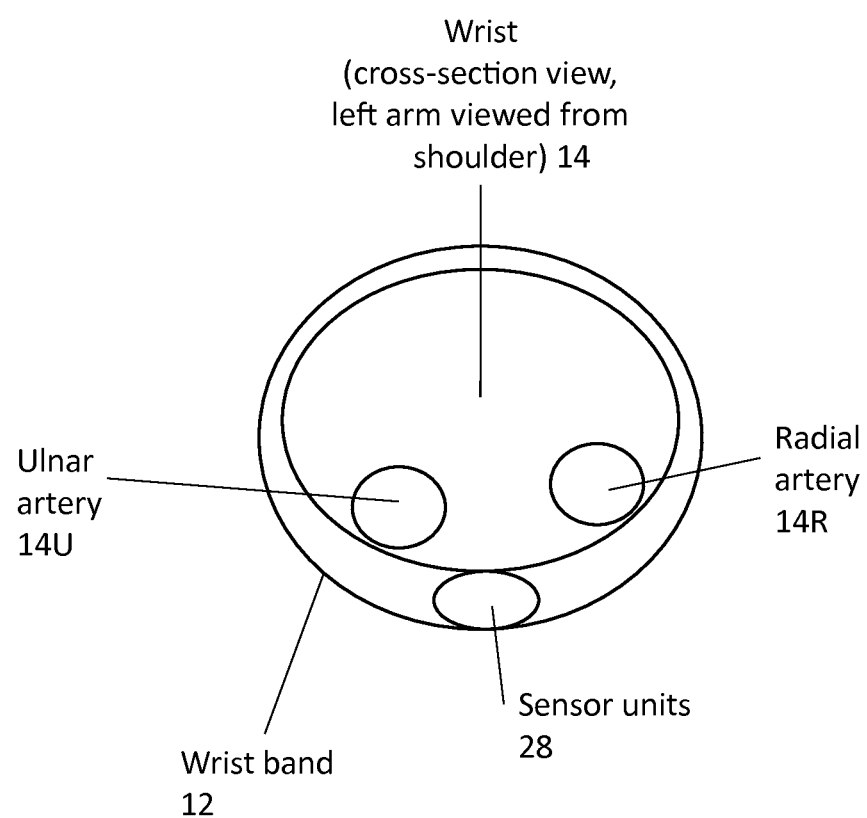
FIG. 5 is a cross-sectional illustration of the wrist with a band mounted sensor in contact for an embodiment used about the wrist.
Figure 6:
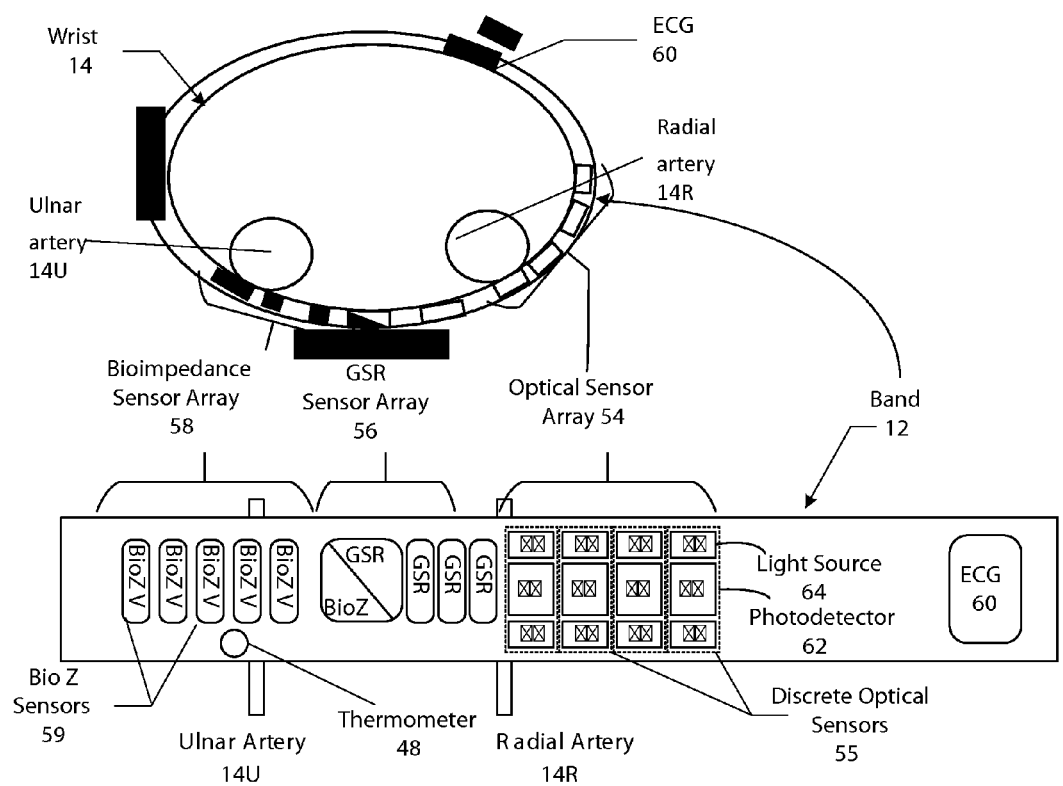
FIG. 6 is a diagram illustrating another embodiment of a modular sensor platform with a self-aligning sensor array system in relation to use about the wrist.

FIG. 5 is a diagram of a cross section of a wrist 14. More specifically, by way of example, FIG. 6 is a diagram illustrating an implementation of a wearable sensor module 10. The top portion of FIG. 6 illustrates the wearable sensor module 10 wrapped around a cross-section of a user's wrist 14, while the bottom portion of FIG. 6 shows the band 12 in an flattened position.

According to this embodiment, the wearable sensor module 10 includes at least an optical sensor array 54, and may also include optional sensors, such as a galvanic skin response (GSR) sensor array 56, a bioimpedance (BioZ) sensor array 58, and an electrocardiogram (ECG) sensor 60, or any combination of which may comprise a sensor array.

According to another embodiment, the sensor units 28 configured as a sensor array(s) comprising an array of discrete sensors that are arranged or laid out on the band 12, such that when the band 12 is worn on a body part, each sensor array may straddle or otherwise address a particular blood vessel (i.e., a vein, artery, or capillary), or an area with higher electrical response irrespective of the blood vessel.

More particularly, as can be seen in FIGS. 5 and 6, the sensor array may be laid out substantially perpendicular to a longitudinal axis of the blood vessel (e.g., radial artery 14R and/or ulnar artery 14U) and overlaps a width of the blood vessel to obtain an optimum signal. In one embodiment, the band 12 may be worn so that the sensor units 28 comprising the sensor array(s) contact the user's skin, but not so tightly that the band 12 is prevented from any movement over the body part, such as the user's wrist 14, or creates discomfort for the user at sensor contact points.

In another embodiment, the sensor units 28 may comprise an optical sensor array 54 that may comprise a photoplethysmograph (PPG) sensor array that may measures relative blood flow, pulse and/or blood oxygen level. In this embodiment, the optical sensor array 54 may be arranged on sensor module 16 so that the optical sensor array 54 is positioned in sufficient proximity to an artery, such as the radial or ulnar artery, to take adequate measurements with sufficient accuracy and reliability.

Further details of the optical sensor array 54 will now be discussed. In general, configuration and layout of each of the discrete optical sensors 55 may vary greatly depending on use cases. In one embodiment, the optical sensor array 54 may include an array of discrete optical sensors 55, where each discrete optical sensor 55 is a combination of at least one photodetector 62 and at least two matching light sources 64 located adjacent to the photodetector 62. In one embodiment, each of the discrete optical sensors 55 may be separated from its neighbor on the band 12 by a predetermined distance of approximately 0.5 to 2 mm.

In one embodiment, the light sources 64 may each comprise a light emitting diode (LED), where LEDs in each of the discrete optical sensors 55 emit light of a different wavelength. Example light colors emitted by the LEDs may include green, red, near infrared, and infrared wavelengths. Each of the photodetectors 62 convert received light energy into an electrical signal. In one embodiment, the signals may comprise reflective photoplethysmograph signals. In another embodiment, the signals may comprise transmittance photoplethysmograph signals. In one embodiment, the photodetectors 62 may comprise phototransistors. In alternative embodiment, the photodetectors 62 may comprise charge-coupled devices (CCD).

Figure 7:
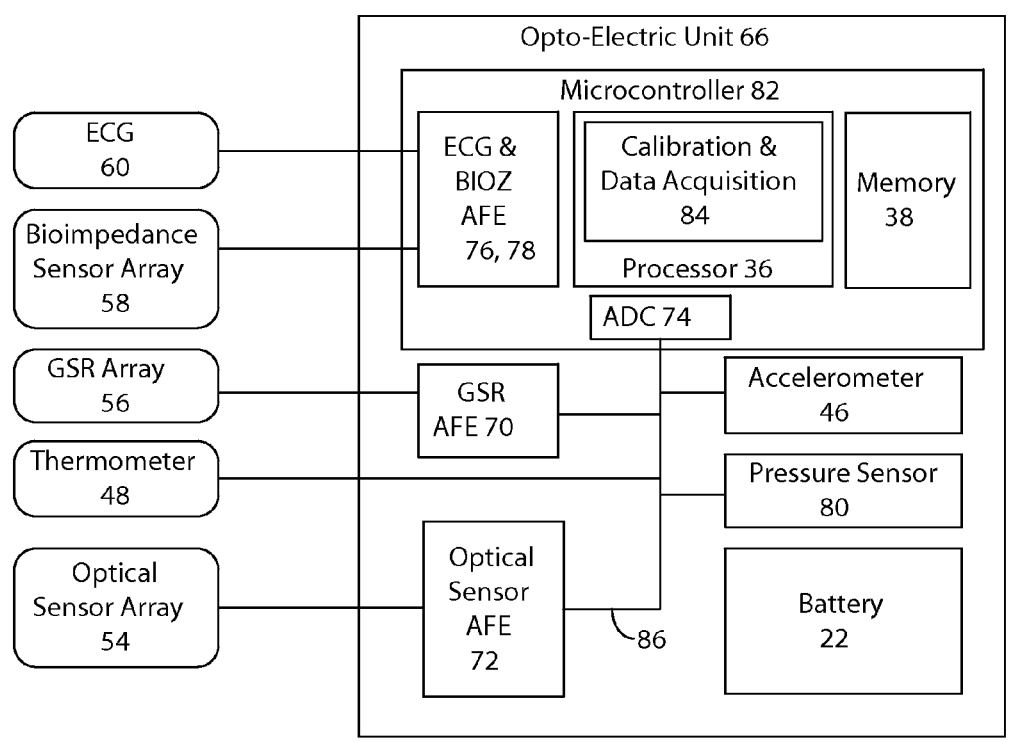
FIG. 7 is a block diagram illustrating components of the modular sensor platform including example sensors and an optical electric unit self-aligning sensor array system in a further embodiment.

FIG. 7 is a block diagram illustrating another configuration for components of wearable sensor module in a further implementation. In this implementation, the ECG 60, the bioimpedance sensor array 58, the GSR array 56, the thermometer 48, and the optical sensor array 54 may be coupled to an optical-electric unit 66 that controls and receives data from the sensors on the band 12. In another implementation, the optical-electric unit 66 may be part of the band 12. In an alternative implementation, the optical-electric unit 66 may be separate from the band 12.

The optical-electric unit 66 may comprise an ECG and bioimpedance (BIOZ) analog front end (AFE) 76, 78, a GSR AFE 70, an optical sensor AFE 72, a processor 36, an analog-to-digital converter (ADC) 74, a memory 38, an accelerometer 46, a pressure sensor 80 and a power source 22.

As used herein, an AFE 68 may comprise an analog signal conditioning circuitry interface between corresponding sensors and the ADC 74 or the processor 36. The ECG and BIOZ AFE 76, 78 exchange signals with the ECG 60 and the bioimpedance sensor array 58. The GSR AFE 70 may exchange signals with the GSR array 56 and the optical sensor AFE 72 may exchange signals with the optical sensor array 54. In one embodiment, the GSR AFE 70, the optical sensor AFE 72, the accelerometer 46, and the pressure sensor 80 may be coupled to the ADC 74 via bus 86. The ADC 74 may convert a physical quantity, such as voltage, to a digital number representing amplitude.

In one embodiment, the ECG and BIOZ AFE 76, 78, memory 38, the processor 36 and the ADC 74 may comprise components of a microcontroller 82. In one embodiment, the GSR AFE 70 and the optical sensor AFE 72 may also be part of the microcontroller 82. The processor 36 in one embodiment may comprise a reduced instruction set computer (RISC), such as a Cortex 32-bit RISC ARM processor core by ARM Holdings, for example. In the embodiment shown in FIG. 7, the memory 38 is an internal memory embedded in the microcontroller 82. In other embodiments, the memory 38 can be external to the microcontroller 82.

According to an exemplary embodiment, the processor 36 may execute a calibration and data acquisition component 84 that may perform sensor calibration and data acquisition functions. In one embodiment, the sensor calibration function may comprise a process for self-aligning one more sensor arrays to a blood vessel. In one embodiment, the sensor calibration may be performed at startup, prior to receiving data from the sensors, or at periodic intervals during operation.

In another embodiment, the sensor units 28 may also comprise a galvanic skin response (GSR) sensor array 56, which may comprise four or more GSR sensors that may measure electrical conductance of the skin that varies with moisture level. Conventionally, two GSR sensors are necessary to measure resistance along the skin surface. According to one aspect of this embodiment, the GSR sensor array 56 is shown including four GSR sensors, where any two of the four may be selected for use. In one embodiment, the GSR sensors 56 may be spaced on the band 2 to 5 mm apart.

In another embodiment, the sensor units 28 may also comprise bioimpedance (BioZ) sensor array 58, which may comprise four or more BioZ sensors 59 that measure bioelectrical impedance or opposition to a flow of electric current through the tissue. Conventionally, only two sets of electrodes are needed to measure bioimpedance, one set for the "I" current and the other set for the "V" voltage. However, according to an exemplary embodiment, a bioimpedance sensor array 58 may be provided that includes at least four to six bioimpedance sensors 59, where any four of electrodes may be selected for "I" current pair and the "V" voltage pair. The selection could be made using a multiplexor. In the embodiment shown, the bioimpedance sensor array 58 is shown straddling an artery, such as the Radial or Ulnar artery. In one embodiment, the BioZ sensors 59 may be spaced on the band 5 to 13 mm apart. In one embodiment, one or more electrodes comprising the BioZ sensors 59 may be multiplexed with one or more of the GSR sensors 56.

In yet another embodiment, the band 12 may include one or more electrocardiogram (ECG) sensors 60 that measure electrical activity of the user's heart over a period of time. In addition, the band 12 may also comprise a thermometer 48 for measuring temperature or a temperature gradient.

According to an exemplary embodiment of an adjustable sensor support structure, a series of sensors supported by flexible bridge structures may be serially connected edge-to-edge along a band. Such a band with bridge supported sensors may be worn, for example, about the wrist 14. When worn about a measurement site such as the wrist 14, the varying topology of the wrist 14 may cause force(s) to simultaneously be exerted upon the bridges due to compliance of the band to the varying topology of the wrist 14.

Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

Gravity is a force. It generally describes how objects interact relative to one another. For example, the gravitational force that the Earth exerts on a person ensures the person remains on the ground. Earth's gravitational force is sometimes referred to as Earth's g-force.

Micro-gravity or hypo-gravity generally refers to a condition where the gravitational force is smaller than that of Earth g-force. For example, the gravitational force exerted by the moon is only a fraction of the gravitational force exerted by the Earth's g-force. By way of another example, when no artificial gravity is present, a person in space flight or on a space station is subject to microgravity. Similarly, super-gravity or hyper-gravity refers to a condition where the gravitational force is larger than that of the Earth's g-force. For example, a person subject to g-forces in a spaceship on takeoff may be subject to super-gravity.

Biological processes are affected by variations in gravitational force. Variations in this force can have an impact on an organism's health and function. For example, the human heart has evolved to pump blood against gravity to the head and upper torso and accept the benefits that Earth's gravity provides in returning the blood to the heart and lungs or pumping blood to the lower extremities. For example, under micro-gravity, the heart's normal pumping function leads to a phenomena called "puffy face syndrome," where the veins of the neck and face appear expanded, the eyes become swollen and red, and the legs grow thinner because the heart does not have the benefit of Earth's gravity and has to pump harder to get blood to the lower extremities and has less help from leg muscles.

As such, human physiological parameters (such as blood flow, blood volume, blood cell production, muscle mass and bone mass, for example) change under depending on what gravitational forces are exerted on the body. It is also known that clocks generally run differently in space—time dilation, and that light may also travel differently.

For example, it is known that blood flow of a jet pilot changes when the fighter jet is flying under varying "g" conditions. Space travel, and the varying gravitational conditions, will affect how blood flows in arteries of human under those conditions, and how some sensors, such as MEMS, measure certain parameters. Additionally, measurements that may employ light, such as the ECG signal, blood pressure and/or blood flow, may depend on time and light array behavior under varying gravitational conditions; that is, the accuracy of those sensors may also be affected by physiological changes and/or how time and light are measured in micro- or super-gravity conditions.

In some embodiments, therefore, the sensors are configured to account for and operate in differing gravitational conditions. For example, the accelerometer/gyroscope 46 may be configured to measure a gravitational force, for example, micro-gravity, experienced by the module 10. The gravitational force measurement or data indicative of the measurement will be fed to one or more of the processor 36, the galvanic skin response (GSR) sensor array 56, the bioimpedance (BioZ) sensor array 58, the electrocardiogram (ECG) sensor 60, and/or the sensor units 28. The processor 36, the galvanic skin response (GSR) sensor array 56, the bioimpedance (BioZ) sensor array 58, the electrocardiogram (ECG) sensor 60, and/or the sensor units 28 may then be calibrated based on the gravitational force data and/or the measurement. Similarly, based on the gravitational force measurement or data indicative of the measurement, the processor 36 may also be configured to determine a time differential and a light speed differential, and send one or more such differentials to one or more of the galvanic skin response (GSR) sensor array 56, the bioimpedance (BioZ) sensor array 58, the electrocardiogram (ECG) sensor 60, and/or the sensor units 28 for further calibration due to time and light measurement differences.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other. Various cloud-based platforms and/or other database platforms may be employed in certain implementations of the modular sensor platform 10 to, for example, receive and send data to the modular sensor platform 10. One such implementation is architecture for multi-modal interactions (not shown). Such architecture can be employed as a layer of artificial intelligence between wearable devices, like modular sensor platform 10, and the larger cloud of other devices, websites, online services, and apps. Such an architecture also may serve to translate (for example by monitoring and comparing) data from the modular sensor platform 10 with archived data, which may be then be used to alert, for example, the user or healthcare professional about changes in condition. This architecture further may facilitate interaction between the modular sensor platform 10 and other information, such as social media, sports, music, movies, email, text messages, hospitals, prescriptions to name a few.

FIGS. 8-12 illustrate several implementations of a modular wearable sensor platform or device 10 showing a removable sensor module 16 mounted on a band 12. The wearable sensor platforms or systems 800, 900, 1000, 1100 and 1200 are analogous to the wearable sensor platforms 10 and thus include analogous components having similar labels. Each of the implementations illustrated may incorporate a removable power source 22, and may include a wireless (or wired) communication capability between the sensor module 16 and the base module 18 or between the sensor module 16 and remote device or system (not shown). Likewise, as would be understood by an artisan, one or more implementations illustrated in FIGS. 8-12 may be employed in the implementations shown in FIGS. 1-3 depending on the desired use.

FIGS. 8-12 illustrate various embodiments that employ configurations that position the sensor module 16 relative to the display 26, such that, as the anthropometric size of the body part increases (or decreases), the sensor module 16 is maintained in its optimal or near optimal position for suitable physiological measurements and user comfort over the period of use, while the display 26 maintains its position in relation to the body part over a large range of anthropometric sizes. For example, when system 10 is worn over the wrist, sensor module 16 maintains an optimal or near optimal position and pressure on the soft, underside of the wrist, while the display 26 maintains a user expected position on the topside of the wrist, regardless range of wrist sizes.

Figure 8:
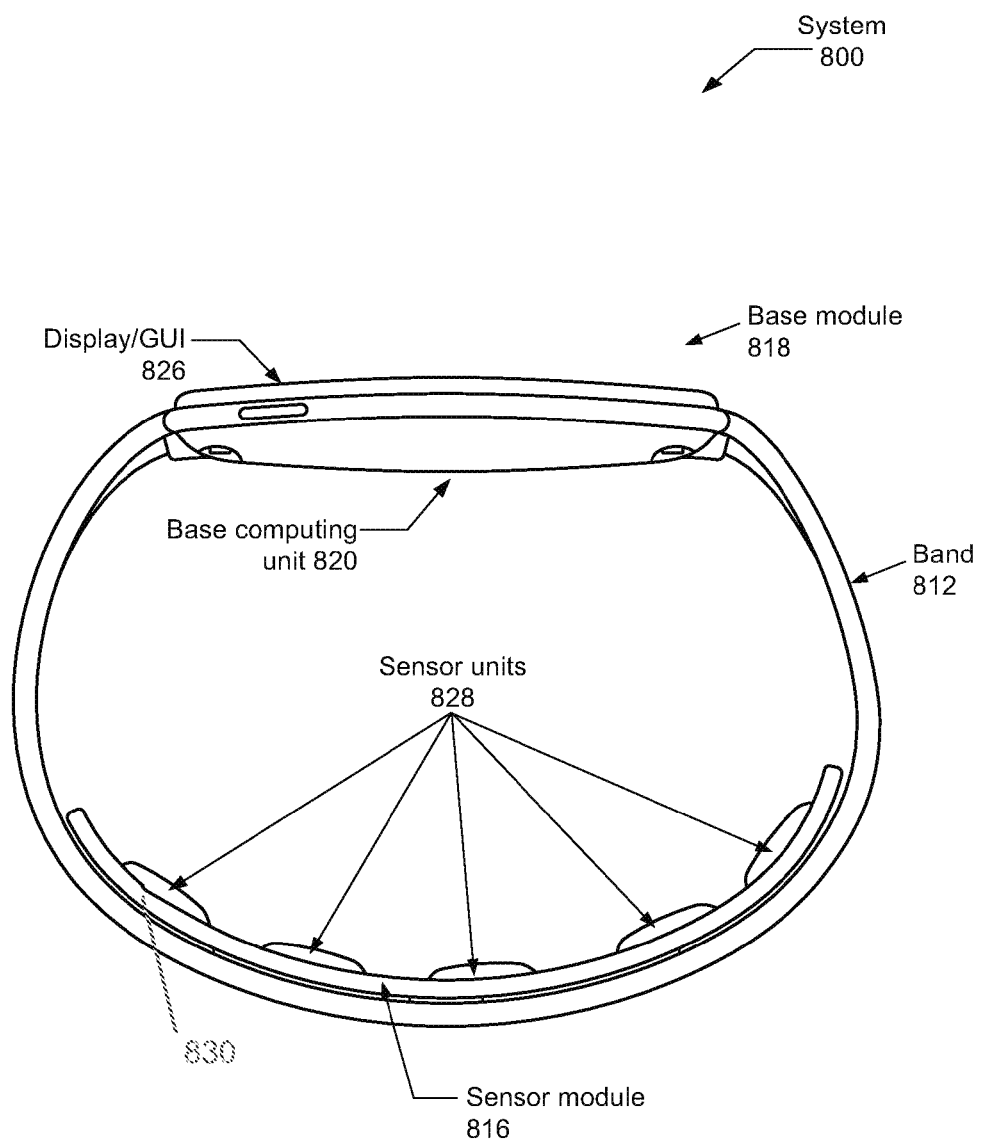
FIG. 8 illustrates an embodiment of a side view of the adjustable wearable system with a sensor module positioned on the band.

More specifically, in the implementation shown in FIG. 8, the sensor module 816 is selectively removable, and further includes a sensor module 816 attached to the band 812, and sensor units (not shown fully) attached to a sensor plate 830. The sensor module 816 also includes a processor or a sensor computing unit (not shown) that is similar to the sensor computing unit 32 of FIGS. 1-3.

The wearable sensor platform or system 800 is illustrated as including an optional smart device or base module 818, a strap or a band 812, a base computing unit 820, a display/GUI 826, and a sensor module 816 attached to the band 812. In some other embodiments, the wearable sensor platform 800 does not include the optional base module 818. In some embodiments, the base module 818 includes an interface (not shown) similar to the communication interface. In some embodiments, the modular wearable sensor platform or system 800 is a smart watch or a smart phone.

In various implementations, the band 812 may be configured to comfortably fit a range of different body parts with varying sizes (e.g., a head, a chest, a wrist, an ankle, a ring) for each unique user. For example, for a wrist, the band 812 may be symmetrically adjustable over a wide range of sizes for band 812 lengths ranging from about 135 mm for a small wrist to about 210 mm for a large wrist, and at the same time maintaining sufficient sensor unit 828 contact with the body part for reliable measurements and user comfort over the period of use (e.g., continuous, short or long-term). Such a band 812 may also include a plurality of sub-bands (not shown) that allows for similar symmetric adjustability around the body part and may also allow for more circulation of air in and around the wrist, thereby providing additional comfort. These sub-bands may be positioned in layers horizontally or vertically. Band 812 may also be of varying elasticity. For example, band 812 may have a less elastic region in or near the base module 818 and/or near the sensor module 816 and a more elastic region in the remaining portions of band 812. Other material properties for band 812 are contemplated and should be appreciated by the artisan.

For example, the band 812 generally consists of chemically inert material, medical-grade material, hypoallergenic silicone, rubber, Graphene, and the like. The band 812 may comprise a material selected from the group consisting of: elastomeric material, non-metallic material, non-magnetic metal, molded plastic, impact-resistant plastic, flexible plastic, plastic, rubber, wood, fabric, cloth, elastomeric material, or combinations of any of the preceding. The band 812 could be also made of a skin graft, artificial skin or other like fabric to provide a continuous skin-like feel and comfort. In some embodiments, the band 812 may employ textile-based wearable form factors (e.g. wrist and palm) made of breathable materials and avoiding hard bulky plastic materials. A flexible fabric could be moved to multiple positions. Such movement could avoid covering the same area of skin for too long with any non-breathable component. As such, a fabric band 812 may further provide added breathability and minimize risks of infection in a system for wearing continuously (24/7 use) in either short-term or longer-term applications. Additionally, the band 812 has a textured interior surface to minimize slipping. Band 812 may also include overlapping or intertwining straps with similar symmetric adjustability.

In the embodiment shown in FIG. 8, both the sensor module 816 and, if employed, the removable power interface 822 (not shown in FIG. 8) are contoured to conform to a body part, here, a wrist of a user. When the system 800 is worn over the wrist, the sensor module 816 may be in contact with the skin of the wrist. In some embodiments, the sensor module 816 is a flexible plate. In some embodiments, the sensor units 828 can be arranged, for example, to be spring loaded or co-molded in a flexible gel, to allow the sensor units 828 to contact the body part without adjusting the band to improve comfort and/or measurement reliability and accuracy. Additionally, the sensor module 816 may be worn with one type of band 812 during the day and inserted into and worn with a different type of band 812 during sleep.

Figure 9:
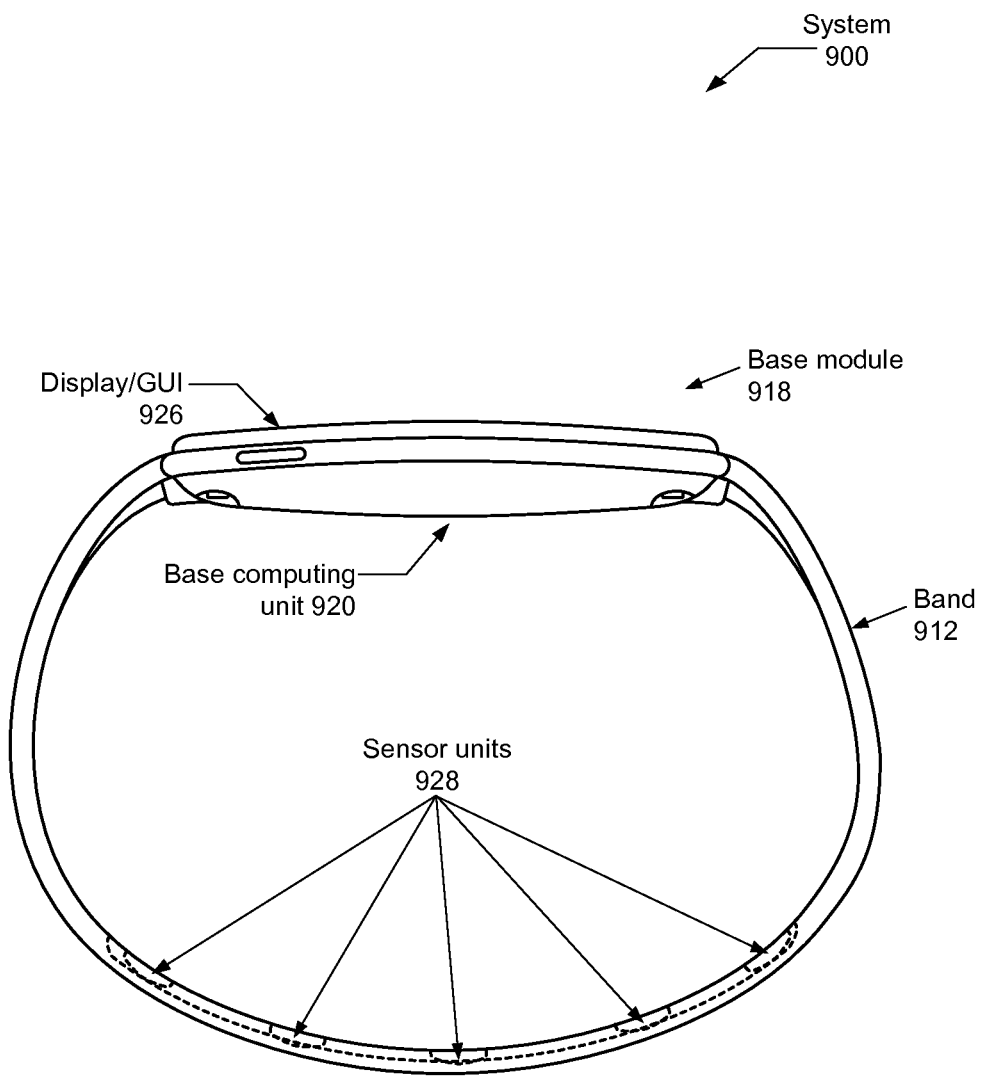
FIG. 9 illustrates a side view of the adjustable wearable system with a sensor module integral to the band.

The system 900 of FIG. 9 is analogous to the wearable sensor platforms 10 and system 800 of FIG. 8. Thus, system 900 includes analogous components having similar labels. In FIG. 9, band 912 in this implementation is similar to band 812. Band 912 employs a sensor module 816 that is co-molded or integral to the band 912. The sensor module 816 can may further have the sensor units 828 arranged in a flexible gel or similar fluid.

Figure 10:
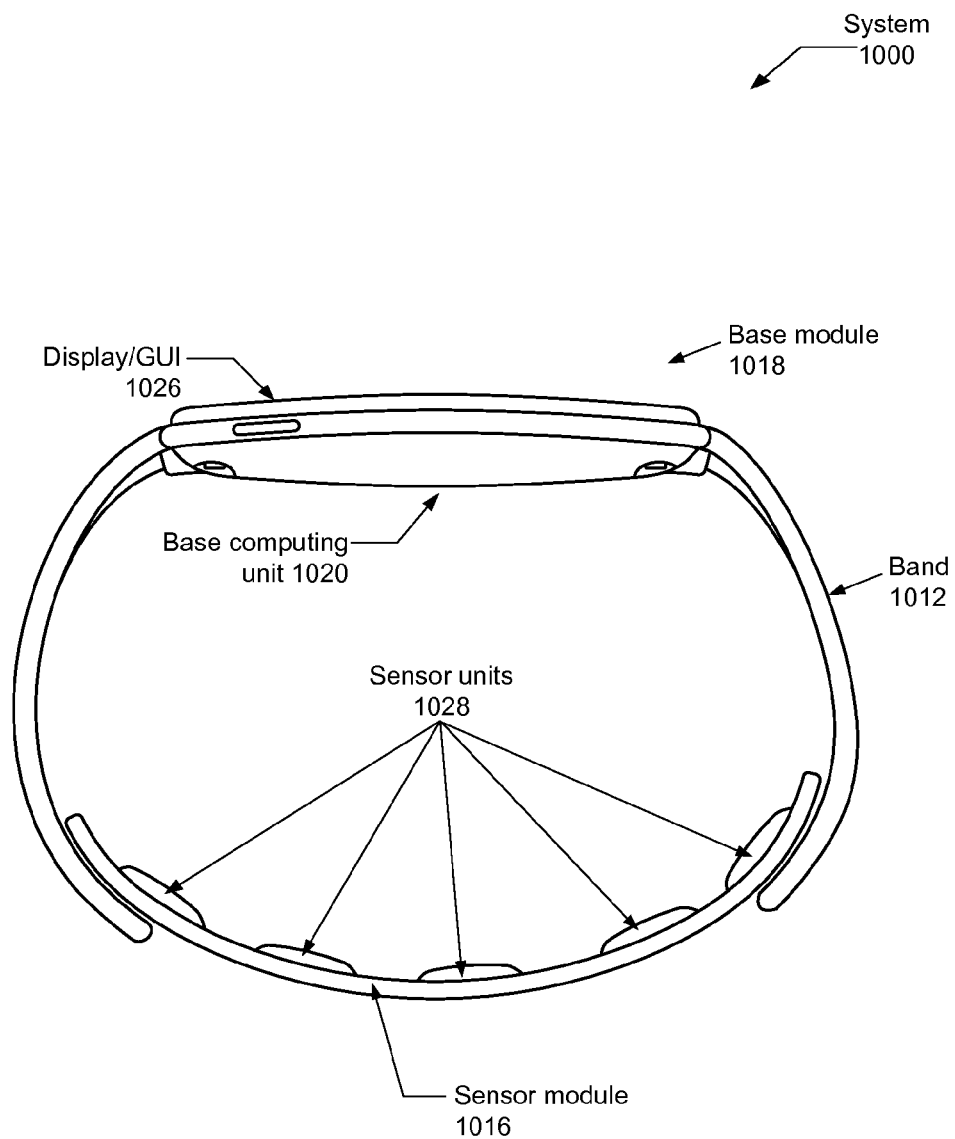
FIG. 10 illustrates a side view of another embodiment of the adjustable wearable system with a sensor module where the band over straps the sensor module.

The system 1000 of FIG. 10 is analogous to the wearable sensor platforms 10 and systems 800 of FIG. 8 and 900 of FIG. 9. Thus, system 1000 includes analogous components having similar labels. In FIG. 10, band 1012 is similar to band 812 and 912. Band 1012 is configured in this implementation as an overstrap arrangement so as to overlap sensor module 1016. Other strap attaching arrangements are contemplated. Band 1012 may be releasably attached to the sensor module 1016, and may be adjustable to accommodate different size of the body parts, while retaining appropriate positioning of the sensor module 1016 relative to the base module 1018. The adjustability of sensor module 1016 can be accomplished through a variety of attachment mechanisms, for example, magnets, ratcheting, grooves, snaps and other ways to hold the sensor module 1016 in position that should be apparent to the artisan.

Figure 11:
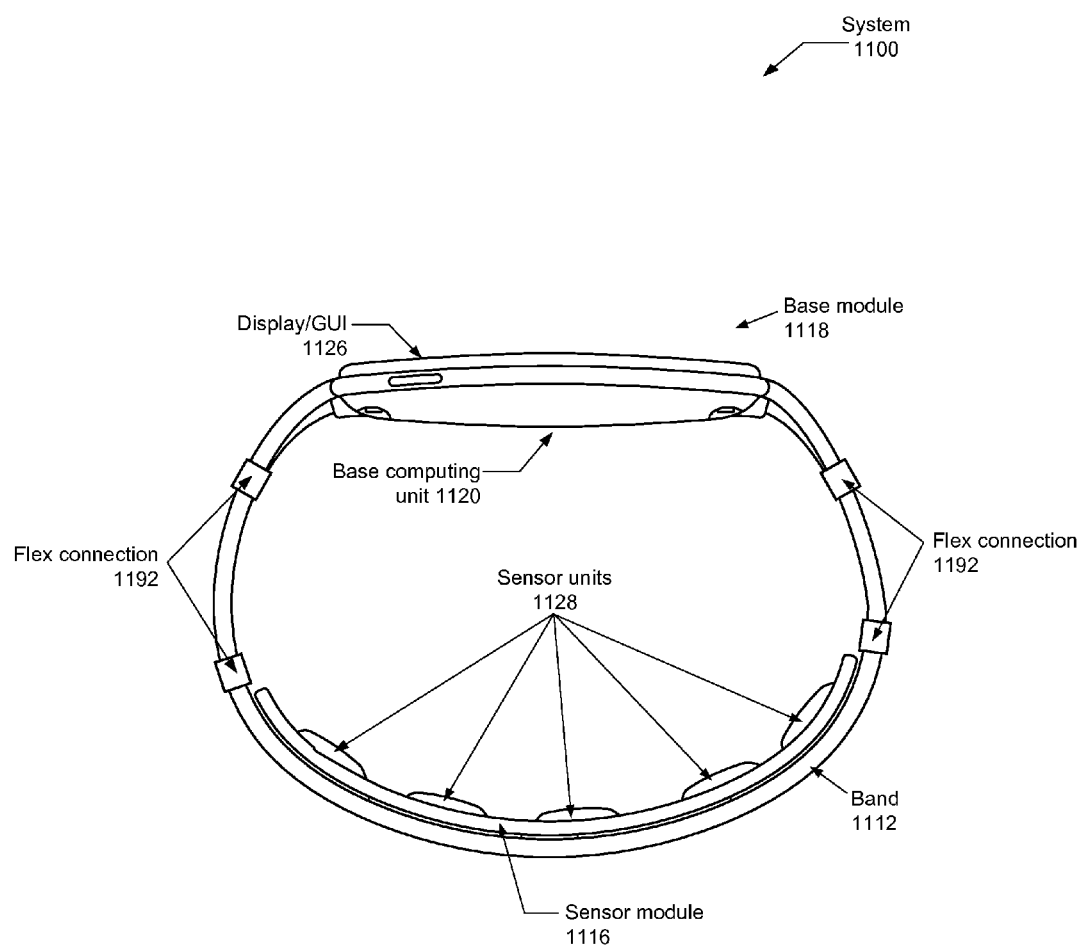
FIG. 11 illustrates a side view of another embodiment of the view of the adjustable wearable system with a modular sensor module with a segmented band connected by flex connections.

The system 1100 of FIG. 11 is analogous to the wearable sensor platforms 10 and systems 800 of FIG. 8, 900 of FIGS. 9 and 1000 of FIG. 10. Thus, system 1100 includes analogous components having similar labels. In FIG. 11, band 1112 is configured in this implementation in a segmented or modular link arrangement. The links of band 1112 are connected by a flex connection 1192. The flex connection 1192 can take a variety of forms. In one implementation, the flex connection 1192 may be a distinct elastic unit attached to the links of band 1112. Such an elastic unit 1192 allows the sensor module 1116 to be positioned relative to the display 1126, such that, as the size of the body part increases (or decreases), the sensor module 1116 is maintained in its optimal or near optimal position for suitable physiological measurements and user comfort over the period of use, while the display 1126 maintains its position in relation to the body part over a large range of anthropometric sizes.

In one implementation, each flex connection 1192 slides into and out of each link of the band 1112. In another implementation, the flex connections 1190 may be integral to the links of the band 1112, where the links of the band 1112, in turn, could be connected by various mechanisms to connect such links, e.g. watch links. In implementations employing links, sizing of the system 1100 about a body part can be further refined by removal or addition of links by a user, for example. Additionally, in implementations including a wireless communication between the sensor module 1116 and the base module 1118, no wiring is needed between the modules, or power-only wiring between the sensor module 1116 and the base module 1118 may be employed. In other implementations, wiring arrangements for power and data communication may be employed between the sensor module 1116 and the base module 1118.

Figure 12:
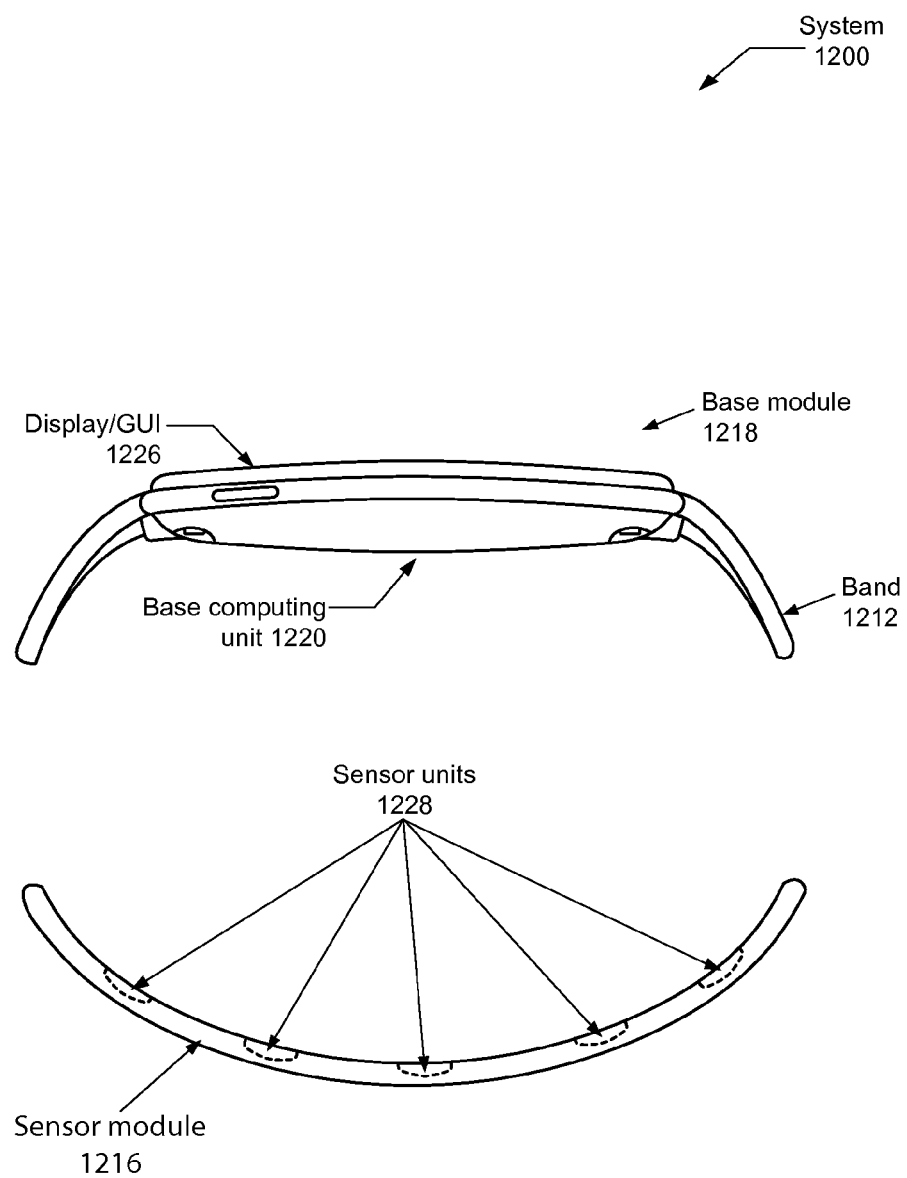
FIG. 12 illustrates another embodiment of view of the adjustable wearable system with a self-adhering sensor module symmetrically disposed from a self-adhering display unit.

The system 1200 of FIG. 12 is analogous to the wearable sensor platforms 10 and systems 800 of FIG. 8, 900 of FIGS. 9 and 1000 of FIGS. 10 and 1100 of FIG. 11. Thus, system 1200 includes analogous components having similar labels. In FIG. 12, the base module 1218 and sensor module 1216 are self-adhering to the body part. In some implementations, a partial band 1212 as shown in FIG. 12 may employed with either the base module 1218 or the sensor module 1216 to further increase the surface area for improved adhesion to the body part. In other implementations, band 1212 is not employed.

It should appreciated that, in some implementations of the wearable sensor platforms 10 and systems 800-1200, the display 1226 may be oriented toward or away from the sensor module 1216. For example, a sensor module 1216 may be applied to the forehead of the user and the display may be oriented toward the user, for example, in the form of glasses for eyewear (not shown) or a helmet face shield (not shown). In other implementations, the sensor module 1216 may be configured as a skin-like tattoo that would adhere the sensor module 1216 to the skin of the forehead (or other body part), while the display 1226 may be a thin, flexible screen applied to the skin of the wrist (or other body part), where both may include a power source.

Figure 13:
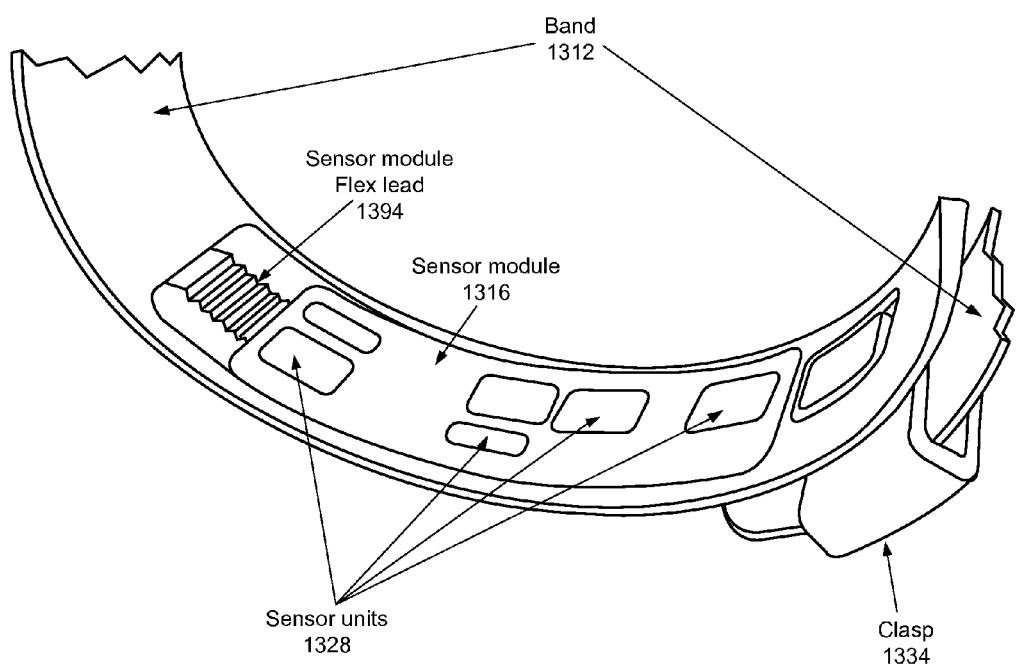
FIG. 13 illustrates a perspective view of an embodiment of the view of the adjustable wearable system with a sensor module comprising a micro-adjustable sensor configuration in a first position.
Figure 14:
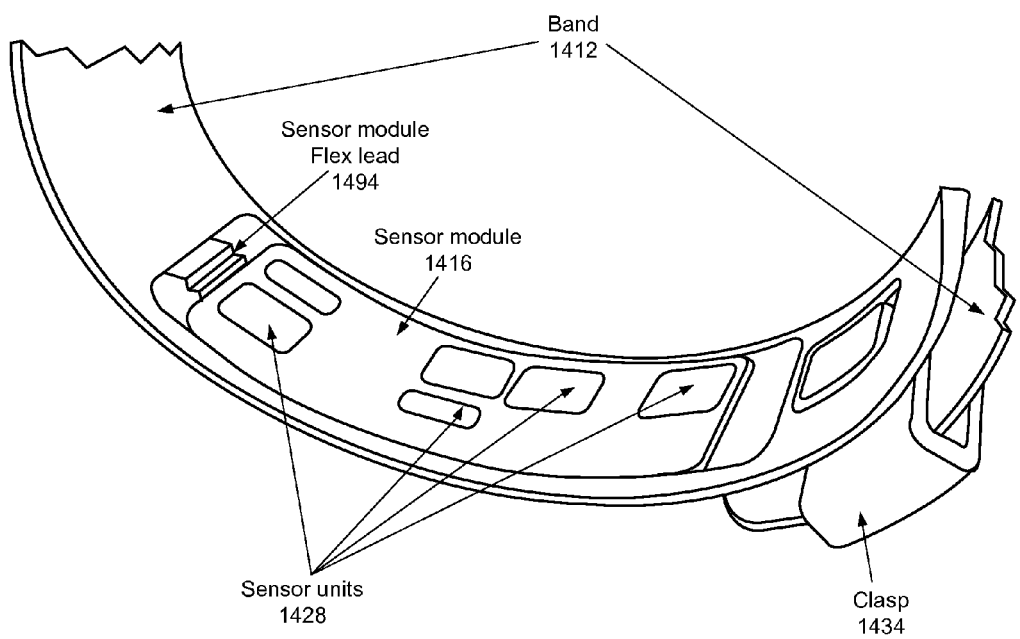
FIG. 14 illustrates another embodiment of the adjustable wearable system with a sensor module comprising a micro-adjustable sensor configuration in a second position relative to that shown in FIG. 13.

FIGS. 13 and 14 illustrate an embodiment using the implementation of FIG. 1, and both FIGS. 13 and 14 include analogous components having similar labels. The implementation of FIGS. 13 and 14 may be employed in other implementations of the wearable sensor platform 10. This implementation may be employed with or without the ECG clasp 1334. In FIG. 13, the sensor module 1316 is arranged to be microadjustable. The micro-adjustable sensor module 1316 of this implementation is positioned in a track in the band 1312. The band 1312 is adjustable, manually or automatically, along the track of the band 1312 via a sensor module flex lead 1394. In this implementation, the sensor module flex lead 1394 is shown as an accordion-like lead that allows adjustment along the track. FIG. 13 illustrates the sensor module 1316 in a first position, while FIG. 14 illustrates sensor module 1416 in a second position relative to the first position in FIG. 13. Various other positions of the sensor module 1316 are possible within the track to accommodate the positioning of the sensor module for a given user.

Figure 15:
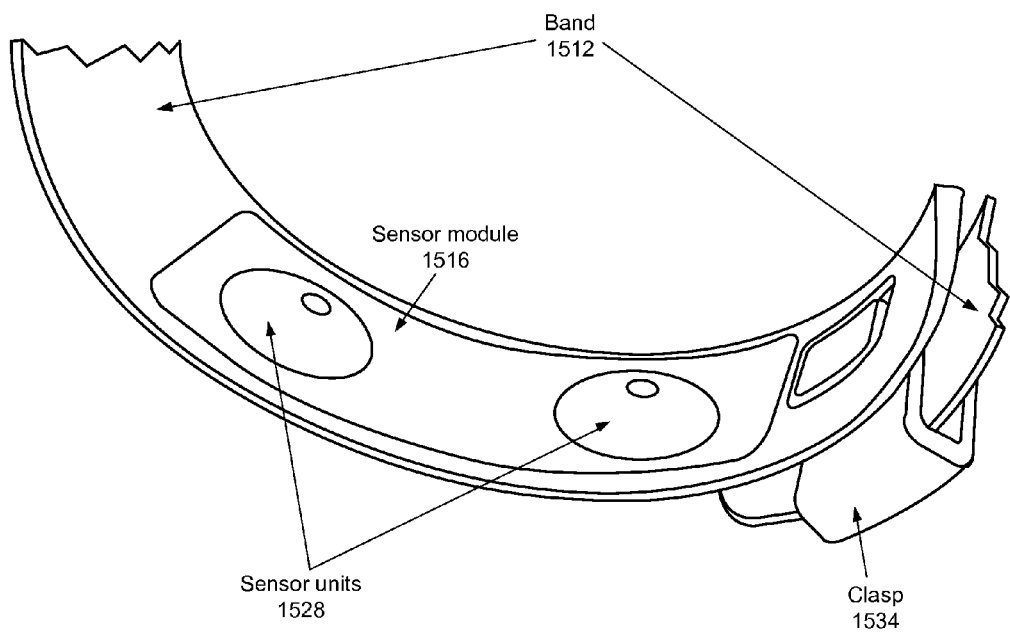
FIG. 15 illustrates a perspective view of an embodiment of the view of the adjustable wearable system with a sensor module comprising a rotatable sensor unit configuration in a first position.
Figure 16:
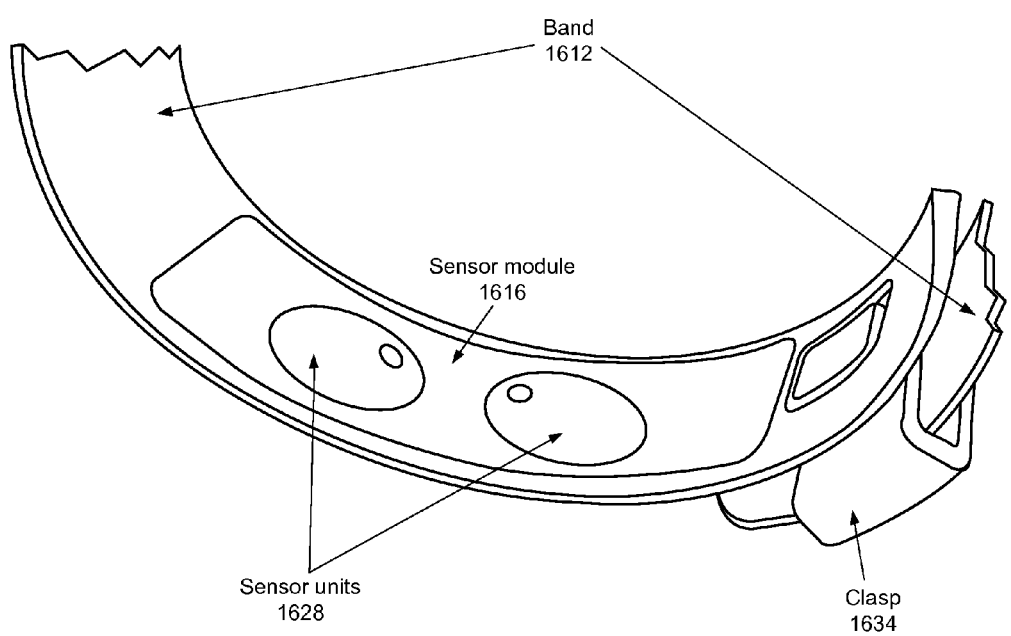
FIG. 16 illustrates another embodiment of the adjustable wearable system with a sensor module comprising a rotatable sensor unit configuration in a second position relative to that shown in FIG. 15.

Additionally, it should be understood that other implementations of the micro-adjustable sensor module 1316 are contemplated. For example, as illustrated in FIGS. 15 and 16, instead of or in addition to employing the flex lead 1394 in FIG. 13 or other configuration for a micro-adjustable sensor module 1316, one or more of the sensor units 1528 may be rotatable, manually or automatically, in the same or opposite rotational directions and the sensor units 1528 may be in sync or out of sync relative to each other depending on the application. Rotation of the sensor units 1528 may occur either individually, in combination with other sensor units 1528 or the sensor module 1516, as illustrated in FIG. 15, sensor module 1616, as illustrated in FIG. 16, may be moved along the track of the band 1512 having a clasp 1534 as illustrated in FIG. 15, and 1612 having a clasp 1634 as illustrated in FIG. 16, and the sensor units 1628 rotated. Such rotation may facilitate refined positioning of the sensor units 1628 for improved comfort or improved physiological measurements depending on the body part.

Figure 17:
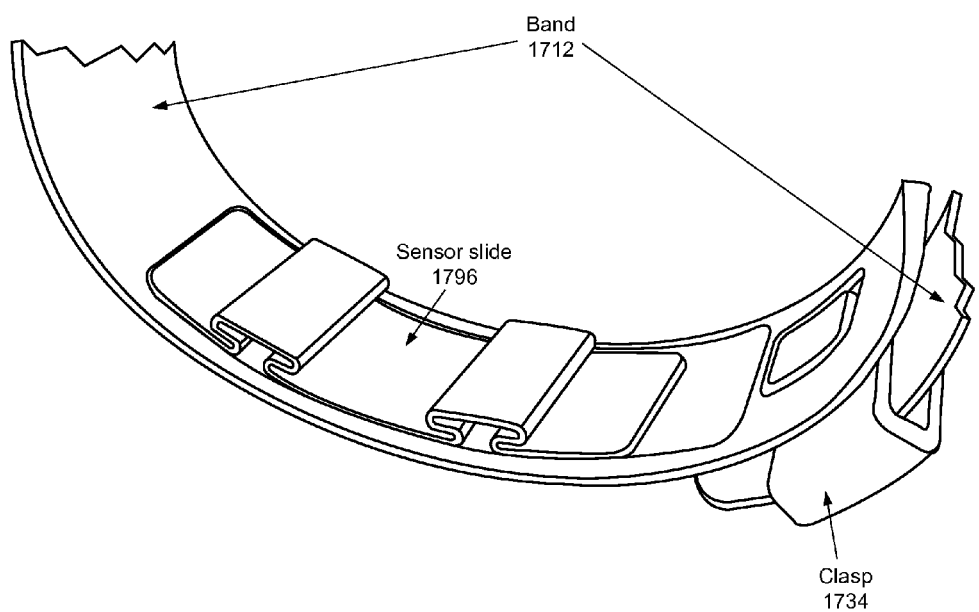
FIG. 17 illustrates a perspective view of an embodiment of the view of the adjustable wearable system with a sensor module comprising a sliding sensor unit configuration in a first position.
Figure 18:
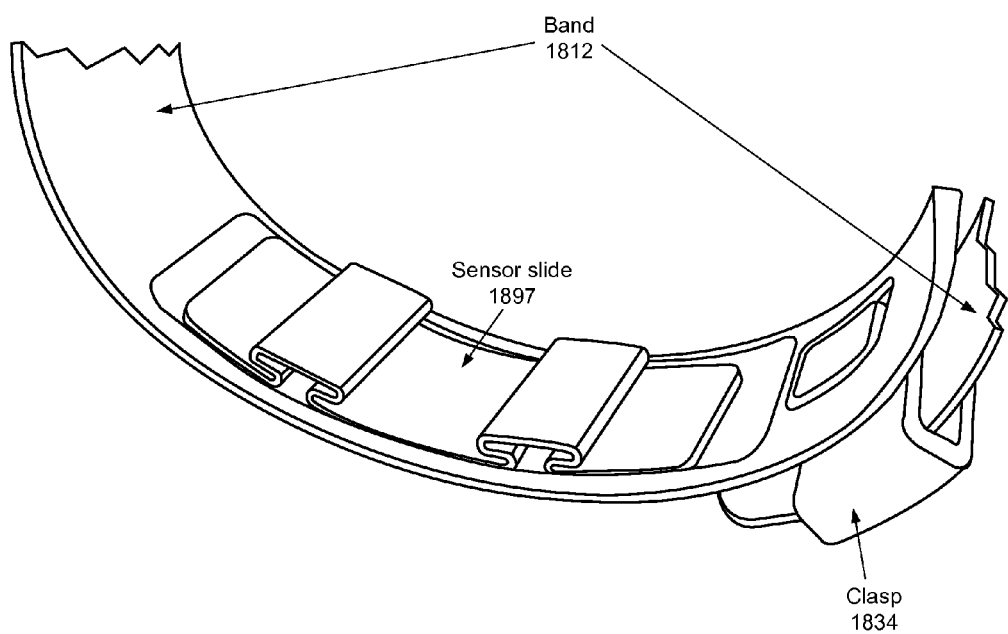
FIG. 18 illustrates another embodiment of the adjustable wearable system with a sensor module comprising a sliding sensor unit configuration in a second position relative to that shown in FIG. 17.

FIGS. 17 and 18 illustrate an embodiment using the implementation of FIG. 1, and both FIGS. 17 and 18 include analogous components having similar labels. The implementation of FIGS. 17 and 18 may be employed in other implementations of the wearable platform 10 (of FIG. 1). In FIG. 17, the micro-adjustable sensor module 16 (of FIG. 1) is arranged on a sensor slide positioned in or on track of band 1712 (1812 of FIG. 18). The micro-adjustable sensor module 16 (of FIG. 1) is positioned adjustably in or on the band 1712 (1812 of FIG. 18) via a sensor slide 1796. In this implementation, the sensor slide 1796 (1897 of FIG. 18) is adjusted, manually or automatically, to refine the position the sensor module 16 (of FIG. 1) as desired. FIG. 17 illustrates the sensor slide 1796 in a first position, while FIG. 18 illustrates sensor slide 1897 in second position relative to the first position in FIG. 17. Various other positions of the sensor slide 1796 are possible within the track to accommodate the positioning of the sensor module 16 (of FIG. 1) for a given user as desired.

Additionally, it should be understood that other implementations of the micro-adjustability of the sensor module 1316 are contemplated. For example, instead of or in addition to employing the flex lead 1394 in FIG. 13, one or more of the sensor units 1328 may be rotatable. Rotation of the sensor units 1328 may occur either individually, in combination with other sensor units 1328 or as the sensor module is moved along the track of the band 1312 in FIG. 13. Such rotation may facilitate refined positioning of the sensor units 1328 for improved comfort or improved physiological measurements depending on the body part. As should be apparent, the various implementations for micro-adjustable sensor module 16 may be employed alone or together depending on the user and application.

The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

Additionally, In addition, the logic flows depicted in the figures do not require the particular order shown, or sequential order, to achieve desirable results. In addition, other steps may be provided, or steps may be eliminated, from the described flows, and other components may be added to, or removed from, the described systems.

Accordingly, other embodiments are within the scope of the following claims.

We claim:

1. A wearable system for measuring physiological data from a device worn about a body part of a user comprising:
   a base module, the base module comprising a display and a base computing unit;
   a sensor module, being spaced apart from the base module, and spatially positioned relative to the base module to establish a contact over the body part for measuring one or more physiological characteristics; and
   the base module being adjustably positioned relative to the sensor module to maintain the contact with the body part for accurate measurements of physiological data regardless of the anthropometric size of the body part.

2. The wearable system of claim 1, wherein the sensor module is positioned over the underside of the wrist of the user.

3. The wearable system of claim 1, where in the sensor module further maintains a pressure contact with the skin of the user to allow for continuous use by the user.

4. The wearable system of claim 1, wherein the sensor module is removable.

5. The wearable system of claim 1, wherein the sensor module is replaceable with a different type of sensor module.

6. The wearable system of claim 5, wherein the sensor module further comprises sensor units and a sensor plate, and wherein the sensor units are removably coupled to the sensor plate, and wherein the sensor units are individually replaceable with different sensor units.

7. The wearable system of claim 1, wherein the sensor module comprises a combination of electric and optical sensors.

8. The wearable system of claim 1, wherein the sensor module comprises one or more of: biological sensors, proximity detectors for detecting the proximity of objects, and environmental sensors.

9. The wearable system of claim 1, wherein the sensor module comprises sensor units that further comprises any combination of optical sensor array, a thermometer, a galvanic skin response (GSR) sensor array, a bioimpedance (BioZ) sensor array, and an electrocardiography (ECG) sensor.

10. The wearable system of claim 9, further comprising a band, and wherein the optical sensor array is arranged on the band to straddle the optical sensor array about a blood vessel.

11. The wearable system of claim 9, further comprising a band, and wherein the bioimpedance (BioZ) sensor array is arranged on the band to straddle the optical sensor array about a blood vessel.

12. The wearable system of claim 1, wherein the base module further includes a base computing unit comprising a processor, memory, a communication interface and a set of sensors.

13. The wearable system of claim 1, further comprising a strap having an interior surface, and wherein the sensor module is removably disposed on the interior surface of the strap.

14. The wearable system of claim 1, further comprising a symmetrically adjustable band, and wherein the symmetrically adjustable band connects the base module and the sensor module.

15. The wearable system of claim 1, further comprising a symmetrically adjustable band, and wherein the symmetrically adjustable band connects the base module and the sensor module, wherein the symmetrically adjustable band is a one-piece band.

16. The wearable system of claim 1, further comprising at least two symmetrically adjustable sub-bands, and wherein the at least two symmetrically adjustable sub-bands connect the base module and the sensor module.

17. The wearable system of claim 1, further comprising at least two symmetrically adjustable sub-bands, and wherein the at least two symmetrically adjustable bands connect the base module and the sensor module, wherein the at least two symmetrically adjustable sub-bands are one-piece bands.

18. The wearable system of claim 1, wherein a symmetrically adjustable band connects the base module and the sensor module, and the sensor module is co-molded to the band.

19. The wearable system of claim 1, wherein a symmetrically adjustable band connects the base module and the sensor module and the sensor module is co-molded to the band in a flexible gel.

20. The wearable system of claim 1, wherein at least two overlapping straps connect the base module and the sensor module.

21. The wearable system of claim 1, wherein a band comprises at least four links connected by a flex connection, and the band connects the base module and the sensor module.

22. The wearable system of claim 1, wherein a band comprises at least four links connected by a flex connection, and the band connects the base module and the sensor module.

23. The wearable system of claim 1, wherein the sensor module comprises sensor units housed on a sensor plate removably coupled to the band.

24. The wearable system of claim 1, wherein the sensor module is positioned on the forehead of the user and the display is oriented toward the user about the head.

25. The wearable system of claim 1, wherein the sensor module adheres to the skin of a body part.

26. The wearable system of claim 25, wherein the sensor module is positioned on the underside of the wrist.

27. The wearable system of claim 1, the base module comprises a thin, flexible display adhered to the skin of a body part.

28. The wearable system of claim 25, wherein the base module is positioned on the top side of the wrist.

29. The wearable system of claim 1, wherein the body part is a wrist and the sizes of the wrist can range from 125 mm to 210 mm.

30. The wearable system of claim 1, wherein the body part is the upper arm, waist, finger, ankle, neck, chest, foot or thigh.

31. The wearable system of claim 1, further comprising a wireless communication unit positioned in the sensor module for transmitting physiological data via a wireless communications link to the base module.

32. The wearable system of claim 1, wherein the sensor module and the base module are connected via a wire for power and communicate data wirelessly.

33. The wearable system of claim 1, further comprising a wireless communication unit for transmitting physiological data via a wireless communications link to the base module and to a location remote from the system.

34. The wearable system of claim 1, wherein the sensor module and the base module each contain battery power sources and communicate wirelessly between each other.

35. The wearable system of claim 1, wherein the sensor module and the base module each contain battery power sources and communicate wirelessly between each other and to a location remote from the system.

36. The wearable system of claim 1, wherein the base module wirelessly communicates with multiple sensor modules worn on different body parts of the user.

37. The wearable system of claim 1, wherein the system further transmits data to a remote architecture for multimodal interactions.

38. The wearable system of claim 37, wherein the architecture comprises a layer of artificial intelligence between the system and one or more of: cloud devices, websites, online services, and applications.

39. The wearable system of claim 37, wherein the system and the architecture communicate changes in user condition.

40. The wearable system of claim 37, wherein architecture interacts with the system to provide information related to social media, sports, music, movies, email, text messages, hospitals and prescriptions.

41. The wearable system of claim 1, wherein the sensor module is a micro-adjustable sensor module.

42. The wearable system of claim 1, further comprising a power source, wherein the power source comprises a removable battery and a permanent battery.

43. A wearable system for measuring physiological data from a device worn about a body part of a user comprising:
 a base module, the base module comprising a display and a base computing unit;
 a micro-adjustable sensor module, having a first sensor and a second sensor, and being spatially positioned relative to the base module and over the body part for measuring one or more physiological characteristics; and
 the micro-adjustable sensor module configured to adjustably refine a position of the first sensor from a first position of the body part of the user, to a second position of the body part, relative to the first position and the second sensor, for sufficient contact with the body part at the second position for accurate measurements of physiological data regardless of the anthropometric size of the body part.

44. The wearable system of claim 43, wherein the sensor module is positioned over the underside of the wrist of the user.

45. The wearable system of claim 43, where in the sensor module further maintains a pressure contact with the skin of the user to allow for continuous use by the user.

46. The wearable system of claim 43, wherein the sensor module is removable.

47. The wearable system of claim 43, wherein the sensor module is replaceable with a different type of sensor module.

48. The wearable system of claim 47, wherein the sensor module further comprises sensor units and a sensor plate, and wherein the sensor units are removably coupled to the sensor plate, and wherein the sensor units are individually replaceable with different sensor units.

49. The wearable system of claim 43, wherein the sensor module comprises a combination of electric and optical sensors.

50. The wearable system of claim 43, wherein the sensor module comprises one or more of: biological sensors, proximity detectors for detecting the proximity of objects, and environmental sensors.

51. The wearable system of claim 43, wherein the sensor module comprises sensor units that further comprises any combination of optical sensor array, a thermometer, a galvanic skin response (GSR) sensor array, a bioimpedance (BioZ) sensor array, and an electrocardiography (ECG) sensor.

52. The wearable system of claim 51, further comprising a band, and wherein the optical sensor array is arranged on the band and configured to straddle the optical sensor array about a blood vessel.

53. The wearable system of claim 51, further comprising a band, and wherein the bioimpedance (BioZ) sensor array is arranged on the band and configured to straddle the optical sensor array about a blood vessel.

54. The wearable system of claim 43, wherein the base module further includes a base computing unit comprising a processor, memory, a communication interface and a set of sensors.

55. The wearable system of claim 43, further comprising a strap having an interior surface, and wherein the sensor module is removably disposed on the interior surface of the strap.

56. The wearable system of claim 43, further comprising a symmetrically adjustable band, and wherein the symmetrically adjustable band connects the base module and the sensor module.

57. The wearable system of claim 43, further comprising a symmetrically adjustable band, and wherein the symmetrically adjustable band connects the base module and the sensor module, wherein the symmetrically adjustable band is a one-piece band.

58. The wearable system of claim 43, further comprising at least two symmetrically adjustable sub-bands, and wherein the at least two symmetrically adjustable sub-bands connect the base module and the sensor module.

59. The wearable system of claim 43, further comprising at least two symmetrically adjustable sub-bands, and wherein the at least two symmetrically adjustable bands connect the base module and the sensor module, wherein the at least two symmetrically adjustable sub-bands are one-piece bands.

60. The wearable system of claim 43, wherein a symmetrically adjustable band connects the base module and the sensor module, and the sensor module is co-molded to the band.

61. The wearable system of claim 43, wherein a symmetrically adjustable band connects the base module and the sensor module and the sensor module is co-molded to the band in a flexible gel.

62. The wearable system of claim 43, wherein at least two overlapping straps connect the base module and the sensor module.

63. The wearable system of claim 43, wherein a band comprises at least four links connected by a flex connection, and the band connects the base module and the sensor module.

64. The wearable system of claim 43, wherein a band comprises at least four links connected by a flex connection, and the band connects the base module and the sensor module.

65. The wearable system of claim 43, wherein the sensor module comprises sensor units housed on a sensor plate removably coupled to the band.

66. The wearable system of claim 43, wherein the sensor module is positioned on the forehead of the user and the display is oriented toward the user about the head.

67. The wearable system of claim 43, wherein the sensor module adheres to the skin of a body part.

68. The wearable system of claim 67, wherein the sensor module is positioned on the underside of the wrist.

69. The wearable system of claim 43, the base module comprises a thin, flexible display adhered to the skin of a body part.

70. The wearable system of claim 69, wherein the base module is positioned on the top side of the wrist.

71. The wearable system of claim 43, wherein the body part is a wrist and the sizes of the wrist can range from 125 mm to 210 mm.

72. The wearable system of claim 43, wherein the body part is the upper arm, waist, finger, ankle, neck, chest, foot or thigh.

73. The wearable system of claim 43, further comprising a wireless communication unit positioned in the sensor module for transmitting physiological data via a wireless communications link to the base module.

74. The wearable system of claim 43, wherein the sensor module and the base module are connected via a wire for power and communicate data wirelessly.

75. The wearable system of claim 43, further comprising a wireless communication unit for transmitting physiological data via a wireless communications link to the base module and to a location remote from the system.

76. The wearable system of claim 43, wherein the sensor module and the base module each contain battery power sources and communicate wirelessly between each other.

77. The wearable system of claim 43, wherein the sensor module and the base module each contain battery power sources and communicate wirelessly between each other and to a location remote from the system.

78. The wearable system of claim 43, wherein the base module wirelessly communicates with multiple sensor modules worn on different body parts of the user.

79. The wearable system of claim 43, wherein the system further transmits data to a remote architecture for multi-modal interactions.

80. The wearable system of claim 79, wherein the architecture comprises a layer of artificial intelligence between the system and one or more of: cloud devices, websites, online services, and applications.

81. The wearable system of claim 79, wherein the system and the architecture communicate changes in user condition.

82. The wearable system of claim 79, wherein architecture interacts with the system to provide information related to social media, sports, music, movies, email, text messages, hospitals and prescriptions.

83. The wearable system of claim 43, further comprising a power source, wherein the power source comprises a removable battery and a permanent battery.

84. A method for measuring physiological data from a wearable device worn about a body part of a user, the wearable device having a base device comprising a display and a base computing unit, and a micro-adjustable sensor module having a first sensor and a second sensor, the method comprising:
spatially and adjustably positioning the micro-adjustable sensor module relative to the base module and over the body part at a first position for measuring one or more physiological characteristics; and
adjustably refining a position of the first sensor of the micro-adjustable sensor module from the first position to a second position of the body part, relative to the first position and to the second sensor, for sufficient contact with the body part at the second position for accurate measurements of physiological data regardless of the anthropometric size of the body part.

85. The method of claim 84, wherein the micro-adjustable sensor module comprises a plurality of sensor units that are rotated to provide sufficient contact with the body part for accurate measurements of physiological data regardless of the anthropometric size of the body part.

86. The method of claim 85, comprising relocating the plurality of sensor units relative to each other to improve contact with the body part for accurate measurements of physiological data.

87. A wearable system of claim 1, wherein the sensor module further comprises a gravitational sensor configured to measure a relative gravitational force, and wherein the sensor module is further configured to calibrate the measurements based on the measured relative gravitational force.

88. A wearable system of claim 87, further comprising a timer configured to adjust a time duration used to measure the physiological characteristics based on the measured gravitational force, wherein the sensor module is further configured to calibrate the measurements based on the adjusted time.

89. A wearable system of claim 87, further comprising a light calibrator configured to adjust light emission based on the gravitational force, wherein the sensor module is further configured to calibrate the measurements based on the adjusted light emission.

90. A wearable system of claim 43, wherein the micro-adjustable sensor module further comprises a gravitational sensor configured to measure a relative gravitational force, and wherein the micro-adjustable sensor module is configured to calibrate the measured physiological data based on the measured relative gravitational force.

91. A wearable system of claim 90, further comprising a timer configured to adjust a time duration used to measure the physiological data based on the measured gravitational force, wherein the micro-adjustable sensor module is further configured to calibrate the measured physiological data based on the adjusted time.

92. A wearable system of claim 90, further comprising a light calibrator configured to adjust light emission based on the gravitational force, wherein the micro-adjustable sensor module is further configured to calibrate the measured physiological data based on the adjusted light emission.

93. A method of claim 84, further comprising:
measuring a relative gravitational force; and
calibrating the physiological data based on the measured relative gravitational force.

94. A method of claim 93, further comprising:
adjusting a time duration used to measure the physiological data based on the measured gravitational force; and
calibrating the physiological data based on the adjusted time.

95. A method of claim 93, further comprising:
adjusting light emission based on the gravitational force; and
calibrating the physiological data based on the adjusted light emission.

* * * * *